(12) United States Patent
Graef et al.

(10) Patent No.: US 6,734,335 B1
(45) Date of Patent: *May 11, 2004

(54) UNITARY ABSORBENT SYSTEM

(75) Inventors: Peter A. Graef, Puyallup, WA (US);
Daniel T. Bunker, Karhula (FI);
Charles E. Miller, Tacoma, WA (US);
Jeffrey D. Mathews, Puyallup, WA (US); Fred B. Howard, Olalla, WA (US); Terry M. Grant, Auburn, WA (US); Shahrokh A. Naieni, Seattle, WA (US); David G. Marsh, Federal Way, WA (US); Melissa L. Dopps, Seattle, WA (US); Kay Rokman, Karhula (FI); Juhani Jansson, Karhula (FI); Eino Laine, Karhula (FI)

(73) Assignee: Weyerhaeuser Company, Federal Way, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/326,213

(22) Filed: Jun. 4, 1999

Related U.S. Application Data

(63) Continuation-in-part of application No. 09/137,503, filed on Aug. 20, 1998, which is a continuation of application No. PCT/US97/22342, filed on Dec. 5, 1997.
(60) Provisional application No. 60/032,916, filed on Dec. 6, 1996.

(51) Int. Cl.$^7$ .............................. A61F 13/15; A61F 13/20
(52) U.S. Cl. ................. 604/365; 428/298.4; 428/300.4; 424/402; 604/327; 604/384; 604/367; 604/378
(58) Field of Search ...................... 424/402; 428/298.4, 428/300.4; 604/327, 378, 365, 367, 383, 384; 442/381, 389, 358, 383, 384, 387, 388, 402

(56) References Cited

U.S. PATENT DOCUMENTS

| 3,716,449 A | 2/1973 | Gatward et al. |
| 3,871,952 A | 3/1975 | Robertson |
| 3,915,791 A | 10/1975 | Langdon |
| 4,145,464 A | 3/1979 | McConnell et al. |
| 4,798,603 A | 1/1989 | Meyer et al. |
| 4,883,707 A | 11/1989 | Newkirk |
| 4,885,204 A | 12/1989 | Bither et al. |
| 4,963,230 A | 10/1990 | Kawase et al. |

(List continued on next page.)

FOREIGN PATENT DOCUMENTS

| EP | 0 496 524 | 7/1992 |
| EP | 0 528 248 | 2/1993 |
| EP | 0 948 951 A2 | 10/1999 |
| WO | WO 96/07783 | 3/1996 |

OTHER PUBLICATIONS

Anonymous, 2244 Research Disclosure, "Thermally Bonded Absorbent Structures Having Discrete, Stepped Density Zones in the Z–Dimension," Jun. 1995, No. 374, Emsworth, GB, 7 pages.
U.S. patent application Ser. No. 60/067,607, Sorebo et al.
Abstract of Costa Rican Patent Application No 5818 (Spanish).
English Translation of Abstract of Costa Rican Patent Application No. 5818.

*Primary Examiner*—Weilun Lo
*Assistant Examiner*—Michele Kidwell
(74) *Attorney, Agent, or Firm*—Christensen O'Connor Johnson Kindness PLLC

(57) ABSTRACT

A unitary absorbent composite having a plurality of strata is disclosed. In the composite, adjacent strata are separated by a transition zone integrally connecting the strata. Each stratum includes fibers and a binder, and the transition zone includes fibers from adjacent strata. Method for forming the unitary composite are also disclosed.

71 Claims, 25 Drawing Sheets

U.S. PATENT DOCUMENTS

| | | |
|---|---|---|
| 4,988,344 A | 1/1991 | Reising et al. |
| 4,988,345 A | 1/1991 | Reising |
| 5,134,007 A | 7/1992 | Reising et al. |
| 5,147,505 A | 9/1992 | Altman |
| 5,164,045 A | 11/1992 | Awofeso et al. |
| 5,178,729 A | 1/1993 | Janda |
| 5,204,173 A | 4/1993 | Canary |
| 5,217,445 A | 6/1993 | Young et al. |
| 5,227,023 A | 7/1993 | Pounder et al. |
| 5,271,987 A | 12/1993 | Iskra |
| 5,290,269 A | 3/1994 | Heiman |
| 5,294,478 A | 3/1994 | Wanek et al. |
| 5,296,290 A | 3/1994 | Brassington |
| 5,360,420 A | 11/1994 | Cook et al. |
| 5,364,382 A | 11/1994 | Latimer et al. |
| 5,409,572 A | 4/1995 | Kershaw et al. |
| 5,429,629 A | 7/1995 | Latimer et al. |
| 5,466,513 A | 11/1995 | Wanek et al. |
| 5,494,554 A | 2/1996 | Edwards et al. |
| 5,522,810 A | 6/1996 | Allen, Jr. et al. |
| 5,531,728 A | 7/1996 | Lash |
| 5,629,069 A | 5/1997 | Hamajima et al. |
| 5,645,542 A | 7/1997 | Anjur et al. |
| 5,653,702 A | 8/1997 | Brohammer et al. |
| 5,820,973 A | 10/1998 | Dodge, II et al. |
| 5,891,119 A | 4/1999 | Ta et al. |
| 5,904,971 A | 5/1999 | Anderson et al. |
| 5,944,706 A | 8/1999 | Palumbo et al. |
| 6,011,195 A | 1/2000 | Muhs et al. |
| 6,020,536 A | 2/2000 | Österdahl et al. |
| 6,022,818 A | 2/2000 | Welchel et al. |

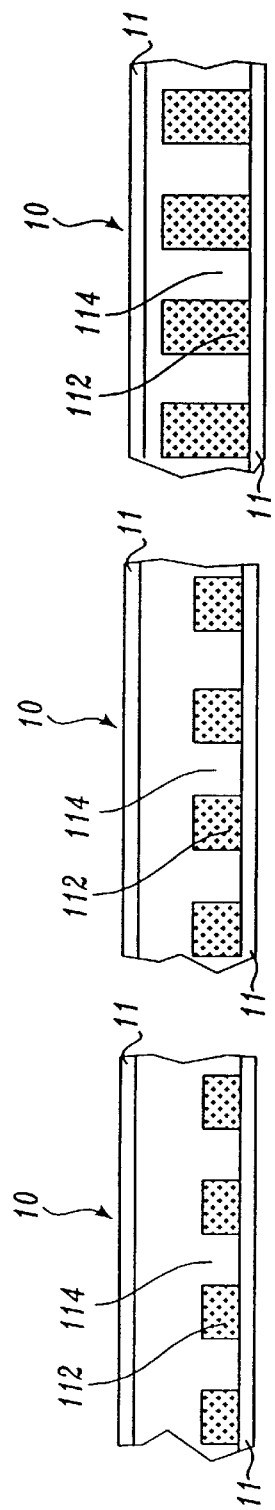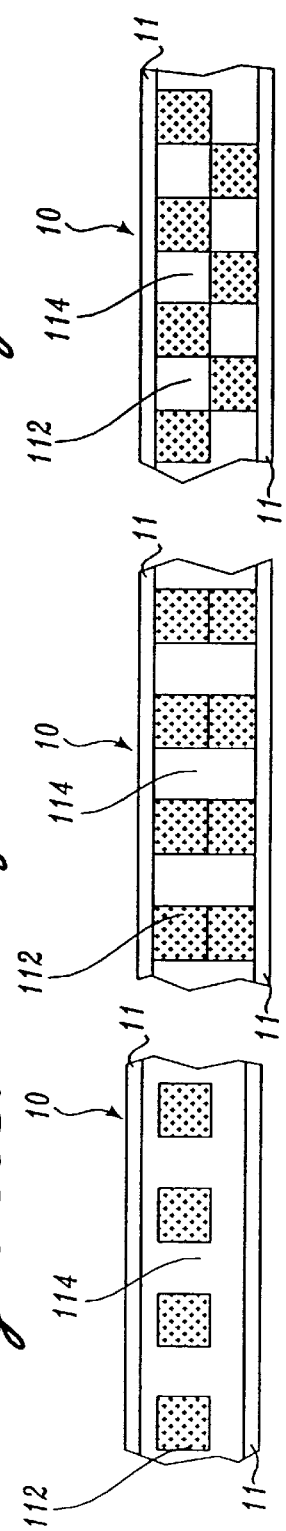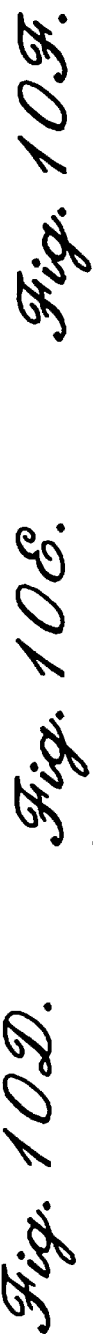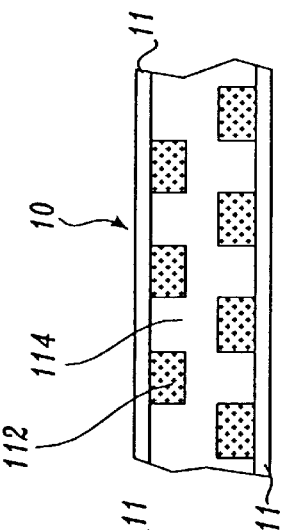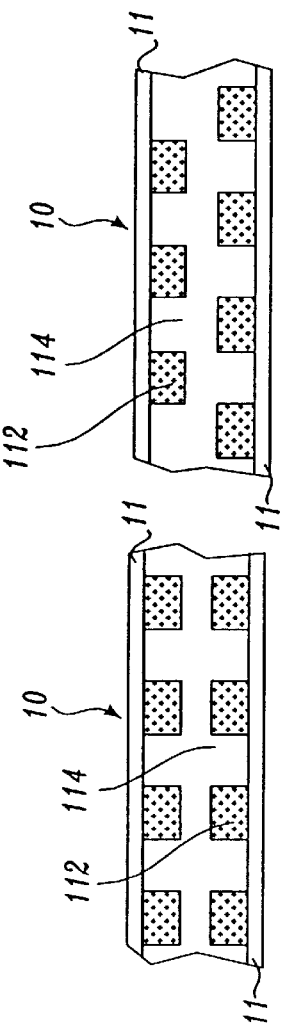

UNITARY ABSORBENT SYSTEM

CROSS-REFERENCE TO RELATED APPLICATIONS

This application is a continuation-in-part of U.S. patent application Ser. No. 09/137,503, filed Aug. 20, 1998, now abandoned, which is a continuation of international patent application Serial No. PCT/US97/22342, filed Dec. 5, 1997, which is a continuation-in-part of U.S. patent application Ser. No. 60/032,916, filed Dec. 6, 1996, priority of the filing dates of which is hereby claimed under 35 U.S.C. §§120 and 119, respectively.

FIELD OF THE INVENTION

The present invention relates generally to multistrata absorbent composites and, in particular, to unitary composites having individual strata separated by transition zones.

BACKGROUND OF THE INVENTION

Currently, diapers are manufactured using individual materials and layers that are designed for a specific functionality. In addition to a liquid pervious topsheet and a liquid impervious backsheet, a typical diaper includes a multilayered absorbent structure. The absorbent structure has an acquisition layer for rapidly acquiring a liquid insult, optionally a distribution layer for receiving and distributing liquid acquired from the acquisition layer, and a storage layer for retaining the acquired liquid. These individual layers are assembled on a production line to provide a diaper having a multilayered absorbent core. Not surprisingly, the nature of the interface between these layers affects the product's performance characteristics and functionality. For diapers assembled on a typical diaper production line, there exists a substantial discontinuity between the materials of each layer resulting in a disruption of the liquid communication between these layers, ultimately impeding liquid transfer between these layers. Problems associated with discontinuities between the materials of adjacent layers is ordinarily reduced by using adhesives. However, adhesives tend to hinder liquid transfer.

Accordingly, there exists a need for an absorbent composite for use in an absorbent articles such as a diaper in which the composite's component layers are in intimate liquid communication such that transfer of liquid between the layers is not hindered. A need also exists for methods for forming such absorbent composites.

SUMMARY OF THE INVENTION

In one aspect, a unitary composite is disclosed that includes a plurality of strata in which adjacent strata are separated by a transition zone integrally connecting the strata. Each stratum of the composite preferably includes fibers and a binder. Each transition zone includes fibers from adjacent strata. Preferred composites include from two to five strata. In other aspects, absorbent articles that incorporate the unitary composite and methods for forming the unitary composite are also disclosed.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein:

FIG. 7 is a diagram illustrating the composition of a representative composite formed in accordance with the present invention through the composite's thickness;

FIGS. 10A–10H are cross-sectional views of representative composites formed in accordance with the present invention;

FIG. 22 is a photomicrograph (12× magnification) of a transition zone of a representative composite produced by a foam-formed method in accordance with the present invention;

FIG. 23 is a photomicrograph (40× magnification) of the transition zone of the representative composite shown in FIG. 22;

DETAILED DESCRIPTION OF THE PREFERRED EMBODIMENT

The composite formed in accordance with the present invention is generally a multistrata composite wherein the interface of each stratum is entangled with the adjacent stratum to form a nonlaminated stratified composite. The absorbent composites formed in accordance with the present invention are in contrast to conventional multilayered composites which are characterized in having abrupt transitions in material compositions at the interfaces of adjacent layers. The absorbent composites of this invention avoid such abrupt material transitions and are characterized by continuous, nonstepwise material gradients in the transition zones between adjacent strata. The transition zone includes the materials of adjacent strata intermixed to a substantial degree. The transition zone integrally and intimately connects adjacent strata of the absorbent composite. The transition zone assures a continuity of material between the zones, and in such composites, the transition from one material composition to another occurs within a band of the total composite thickness.

In one aspect, the present invention provides an absorbent composite that is a unitary structure which includes two or more strata. The term "unitary" refers to the composite's structure in which adjacent strata are integrally connected through a transition zone to provide a structure with adjacent strata in intimate fluid communication.

In the composite, transition zones separate the composite's strata. The nature of the transition zone can vary from composite-to-composite and from stratum-to-stratum within a composite. The transition zone can be designed to satisfy the performance requirements of a particular composite. In general, the transition zone integrally connects adjacent strata and provides for intimate liquid communication between strata. The transition zone includes fibers from one stratum extending into the adjacent stratum. For a composite having two strata, the transition zone includes fibers from the first stratum extending into the second stratum and fibers from the second stratum extending into the first stratum.

Transition zone thickness within a composite can be widely varied depending on the composite. Absorbent composites of the present invention can include a transition zone that is relatively thin. Absorbent composites that include such thin transition zones have fairly abrupt transitions in material composition between strata. Alternatively, the composite can include a transition zone that is gradual such that the transition from one zone to the next occurs over a relatively greater thickness of the composite. In such a composite, the material compositions of each zone are intermixed to a significant extent resulting in rather extended composition gradients.

Figure 1A:
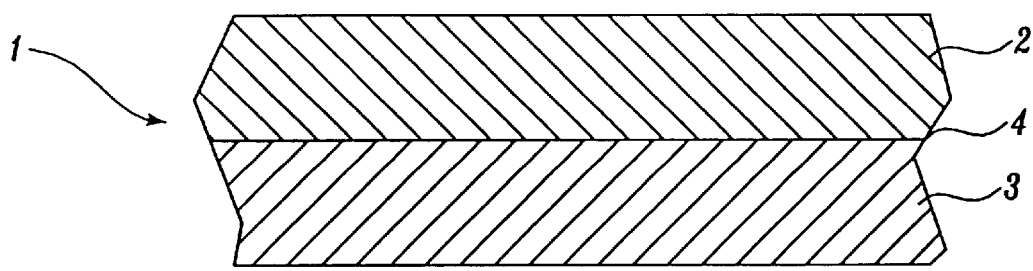
FIG. 1A is a cross-sectional view of a conventional absorbent structure having two layers.
Figure 1B:
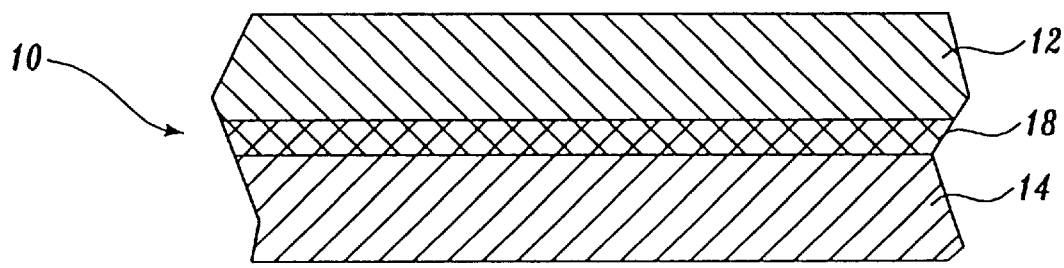
FIGS. 1B–1D are cross-sectional views of representative composites formed in accordance with the present invention.
Figure 1C:
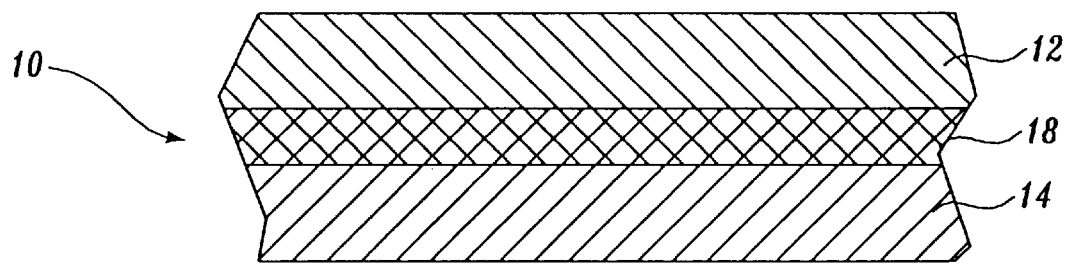
Figure 1D:
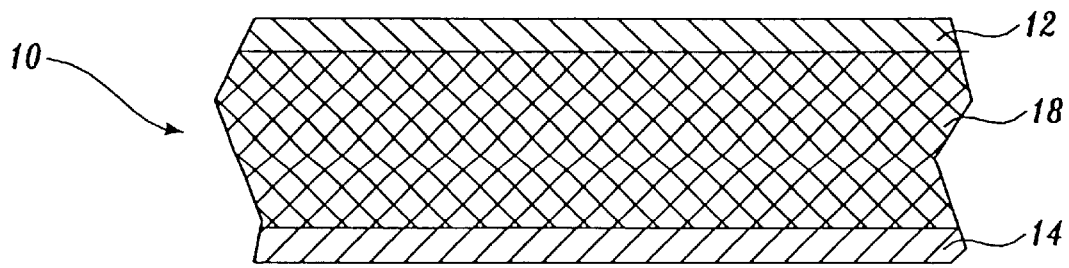
Figure 2A:
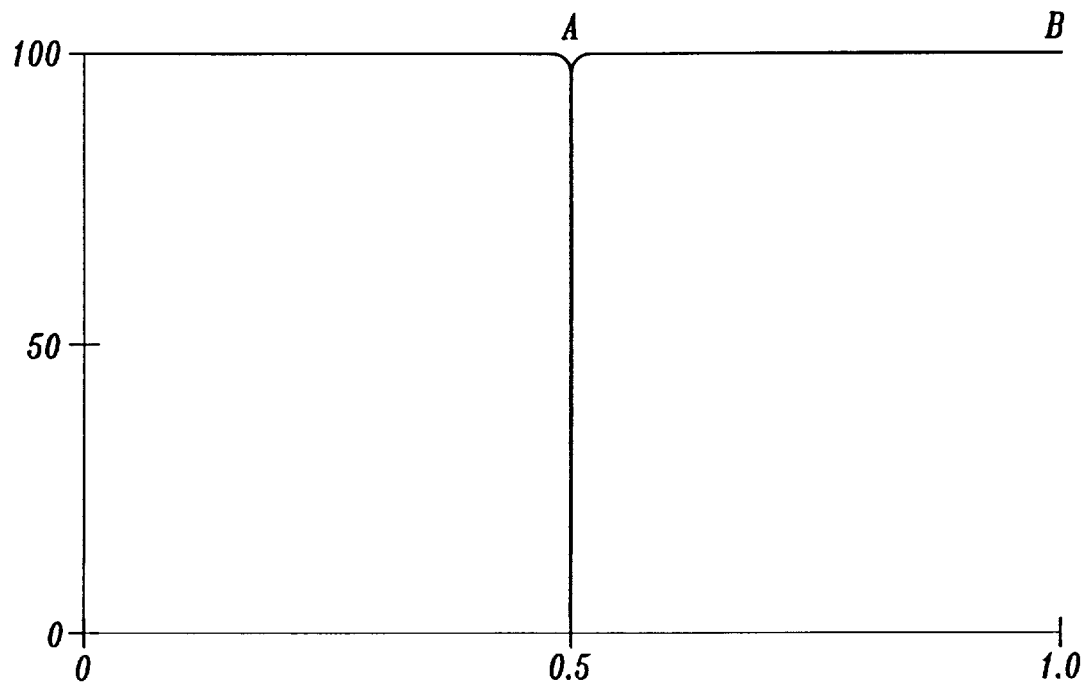
FIG. 2A is a diagram illustrating the composition of a conventional absorbent structure through the structure's thickness.
Figure 2B:
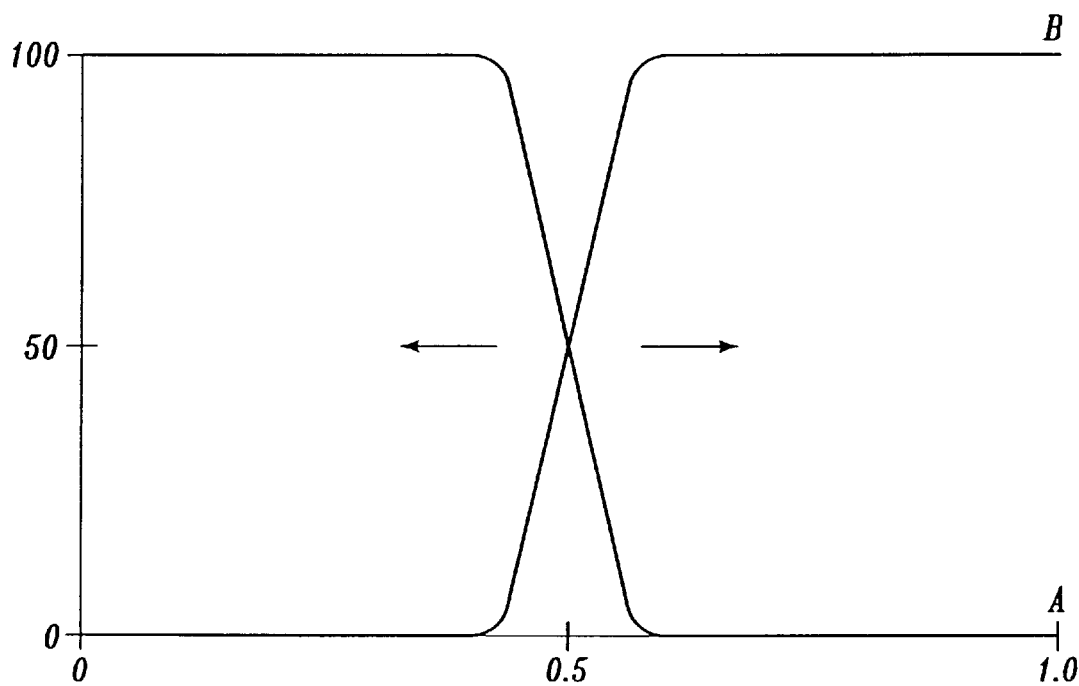
FIGS. 2B–D are diagrams illustrating the composition of representative composites formed in accordance with the present invention through the composite's thickness.
Figure 2C:
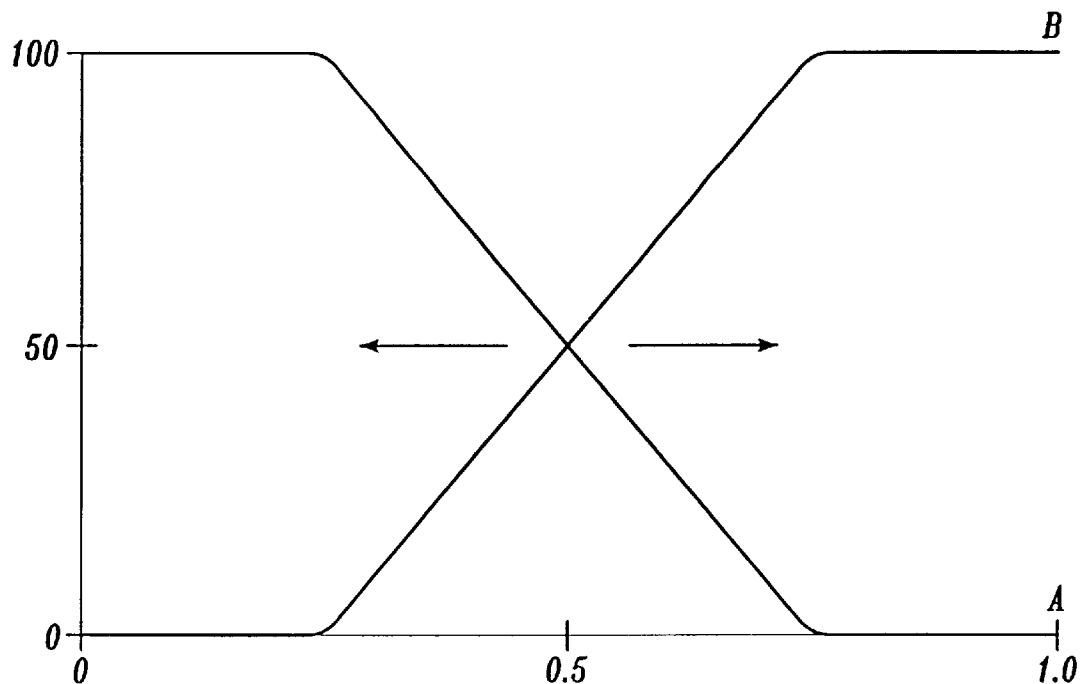
Figure 2D:
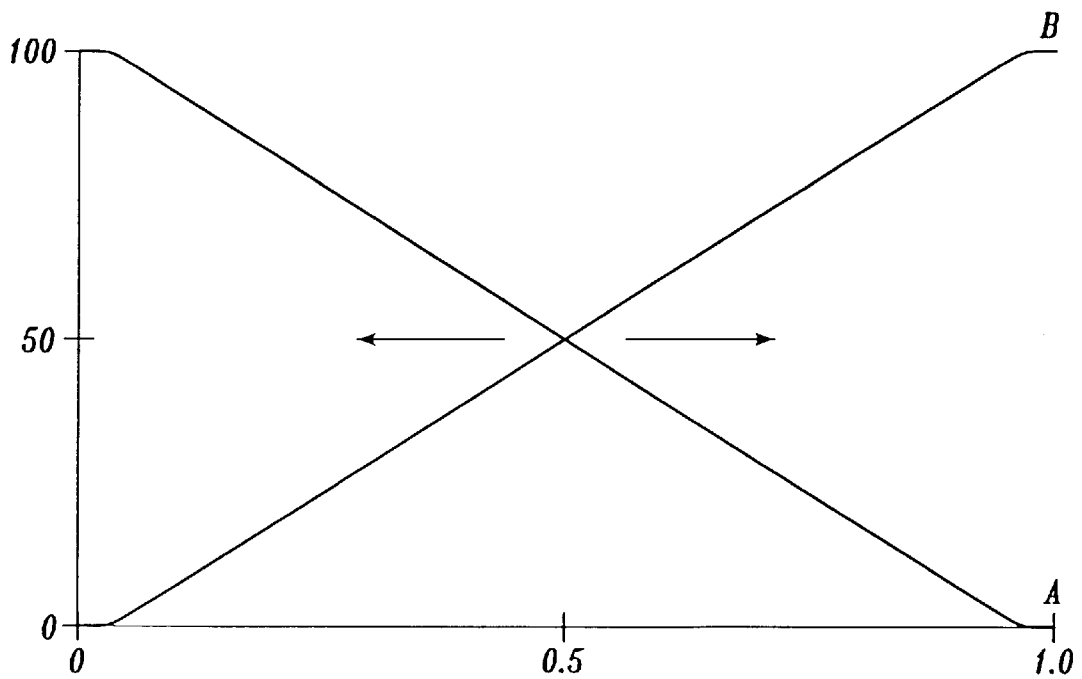
Figure 1:
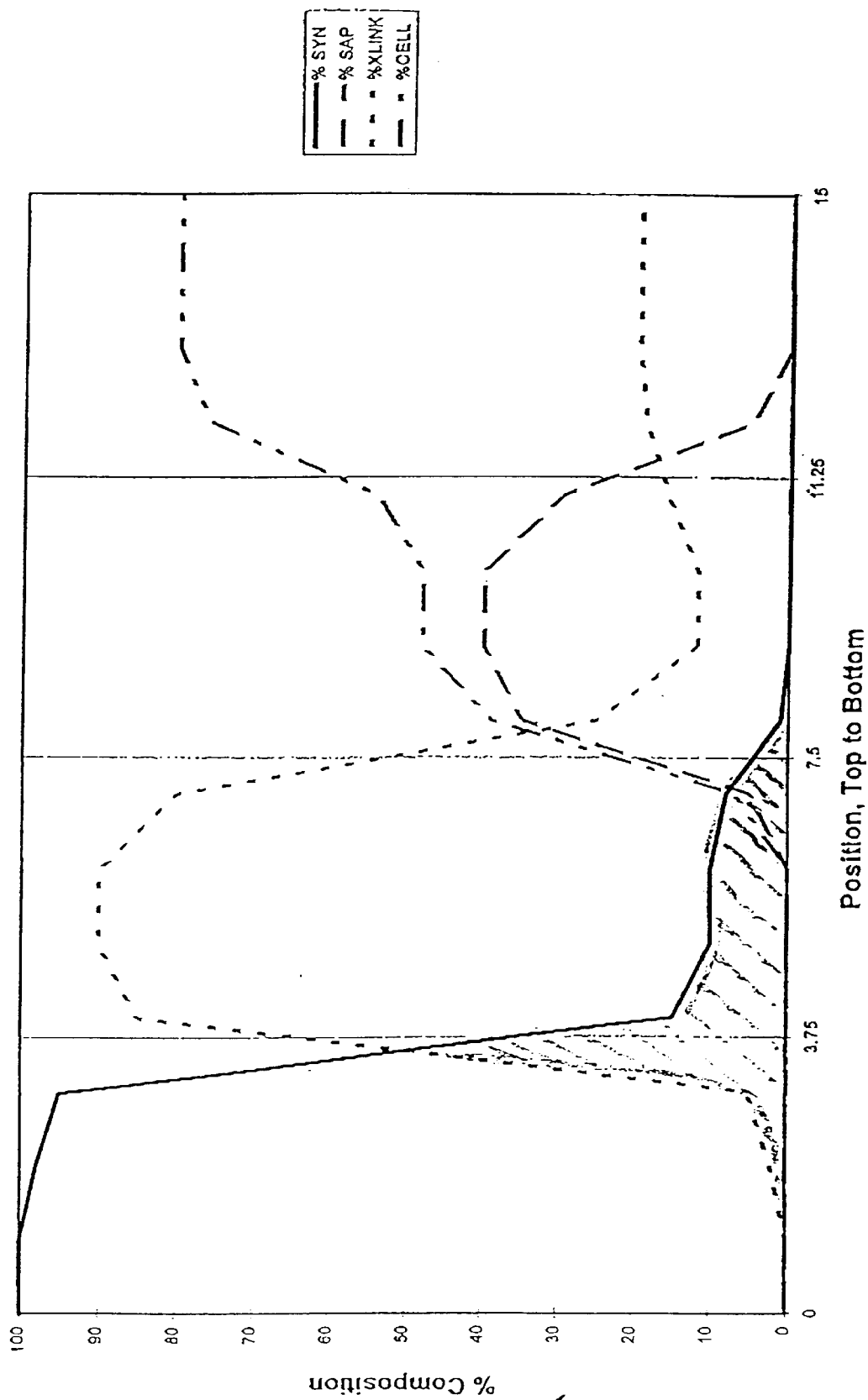

The structures of representative unitary composites of the present invention and a conventional absorbent bilayer are illustrated schematically in FIG. 1. A conventional absorbent composite having a bilayer construction is illustrated in FIG. 1A. Referring to FIG. 1A, conventional absorbent structure 1 includes first layer 2 adjacent second layer 4 and interface 3. In contrast to the illustrated conventional structure having an interface separating layers, the composites of the invention include a transition zone. Referring to FIGS. 1B–1D, representative composites 10 include first stratum 12 and second stratum 14 joined through transition zone 18. Transition zone 18 includes the materials from strata 12 and 14. As noted above, the transition zone thickness can be varied. Transition zone 18 in FIG. 1B has a thickness less than the transition zone illustrated in FIG. 1C, which has a thickness less than the transition zone shown in FIG. 1D.

Composition/thickness profiles for the composites illustrated in FIG. 1 are shown in FIG. 2. In these profiles, the first stratum composition A and the second stratum composition B range from 0 to 100 percent based on the total composite as a function of composite thickness (i.e., from the composite's upper surface to its lower surface). The profile shown in FIG. 2A corresponds to the conventional structure of FIG. 1A. As illustrated in the profile of FIG. 2A, the conventional structure has an interface between adjacent strata. At the interface, the structure's composition abruptly changes from 100 percent A to 100 percent B. The profiles of FIGS. 2B–2D correspond to the representative composites illustrated in FIGS. 1B–1D. Referring to FIGS. 2B–2D, these profiles illustrate the change in the composite's composition through the composite's transition zone. As illustrated in these profiles, the transition zone originates as the composite composition changes from 100 percent A and terminates as the composite composition reaches 100 percent B. As for FIGS. 1B–D, the transition zones illustrated in FIGS. 2B–D having increasing length. In these profiles, the representative composites have transitions zones centered at the center of the composite's thickness. As indicated by the arrows in these profiles, representative composites of the invention can have transition zones centered throughout the composite's thickness.

Although FIGS. 1 and 2 illustrate representative composites having only two strata and a single transition zone, composites can include additional strata (e.g., three, four, or five or more strata) and transitions zones. It will be appreciated that although FIG. 2 illustrates the composition of a representative unitary composite having two strata and a transition zone, similar diagrams can be made illustrating composites formed in accordance with the present invention having more than two strata and more than one transition zone.

The composites formed in accordance with the present invention include two or more strata with adjacent strata separated by a transition zone. The composites of the invention are preferably formed by a method that includes depositing a fibrous furnish on a foraminous support. In one method, the composite's strata can be formed through the use of a divided or multichanneled headbox. For forming composites having two strata, a headbox divided having first and second chambers can be used. The first stratum can be formed from a first fibrous furnish introduced into a first headbox chamber, and the second stratum can be formed from a second fibrous furnish introduced into a second headbox chamber. The deposition of the headbox contents (e.g., from the first and second chambers) onto a foraminous support provides a web that, on dewatering and drying, results in a representative composite of the invention, a unitary composite having two strata separated by a transition zone. For the composite described above, the composite's transition zone results from the mixing of the first and second fibrous furnishes (e.g., in the headbox) and includes materials from both furnishes. The composite's transition zone thickness can be controlled by the headbox. In the divided headbox described above, the first and second furnish mix to an extent prior to exiting the headbox and ejection onto the foraminous support. The greater the mixing prior to ejection from the headbox, the greater the transition zone.

Figure 3A:
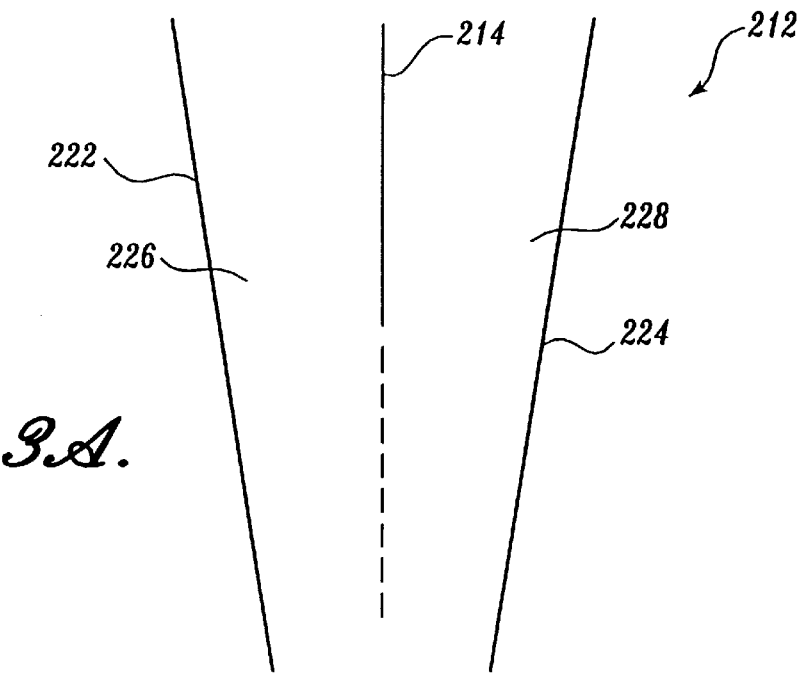
FIG. 3A is a diagram of a divided headbox for forming a representative composite according to the present invention.
Figure 3B:
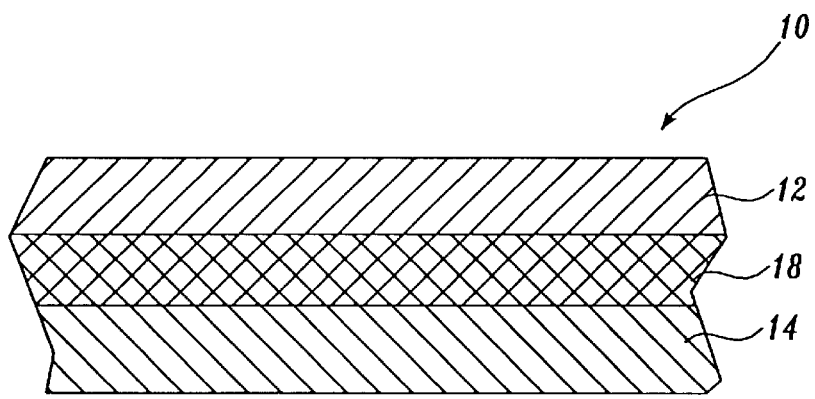
FIGS. 3B and 3C are cross-sectional views of representative composites formed in accordance with the present invention.
Figure 3C:
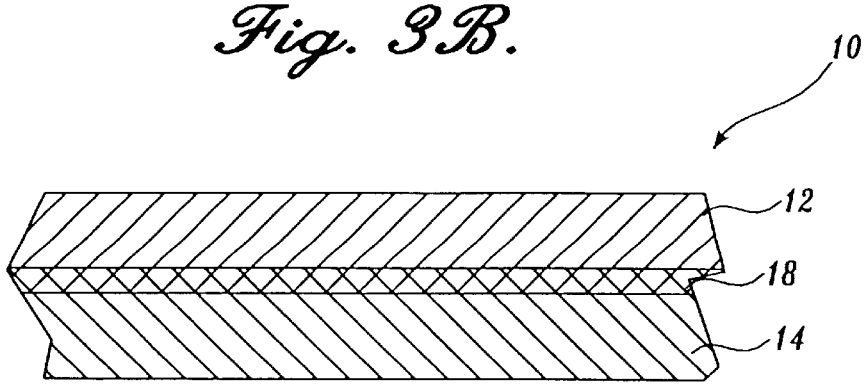

A schematic diagram of a divided headbox having two chambers is illustrated in FIG. 3A. Referring to FIG. 3A, headbox 212 includes walls 222 and 224 and divider 214 creating first chamber 226 and second chamber 228. The length of divider 214 can be varied such that the point at which a furnish introduced into chamber 226 meets and commences mixing with a furnish introduced into chamber 228. The variance in the length of divider 214 is depicted as the dashed line in FIG. 3A. The extent of furnish mixing and, therefore, the thickness of the transition zone can be controlled by the adjusting the point at which the fibrous furnishes mix within the headbox (e.g., divider length). In general, the lesser the furnish mixing, and the thinner the transition zone in the resulting composite and, conversely, the greater the furnish mixing, the thicker the transition zone. Representative composites formed in accordance with the present invention by varying the point of furnish mixing are illustrated in FIGS. 3B and 3C. FIGS. 3B and 3C show representative composites 10 having first stratum 12, second stratum 14, and transition zone 18. The thicker transition zone 18 in FIG. 3B compared to the thinner transition zone 18 in FIG. 3C results from forming using the headbox of FIG. 3A and using a relatively shorter divider 214.

FIGS. 4–6 illustrate headboxes having two, three, and four dividers, respectively, to provide representative composites of the invention having three, four, and five strata, respectively.

Figure 4A:
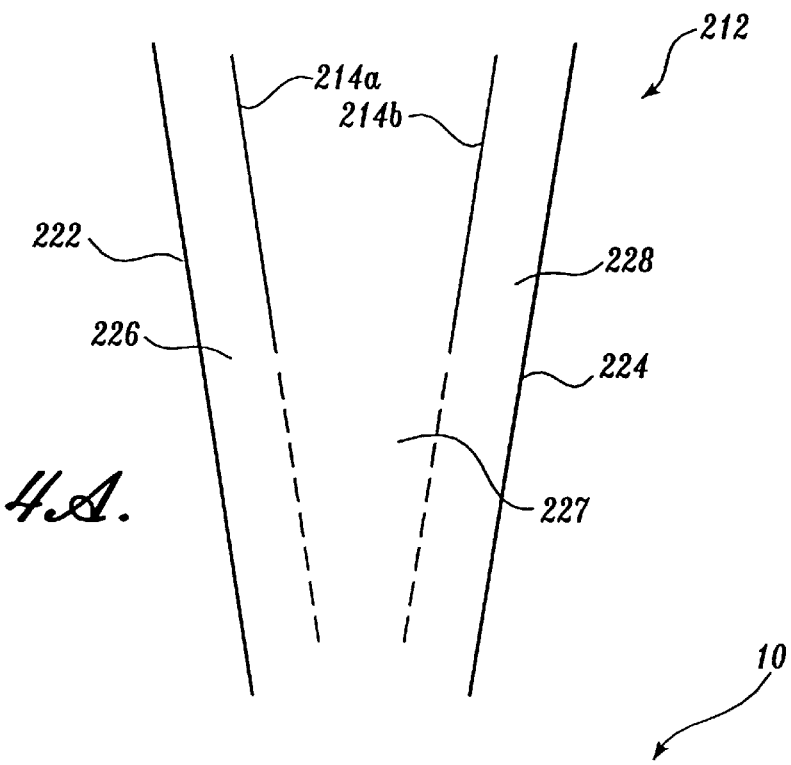
FIG. 4A is a diagram of a divided headbox for forming a representative composite according to the present invention.
Figure 4B:
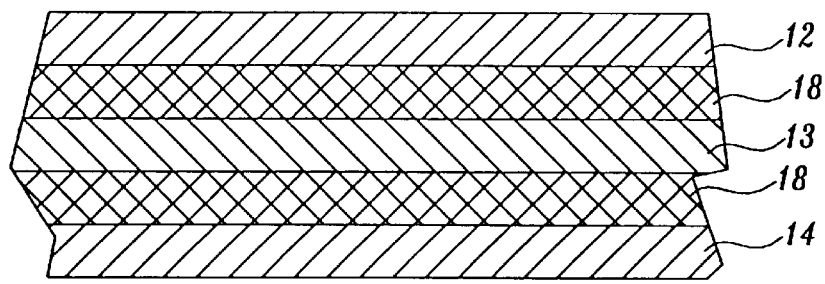
FIGS. 4B–4D are cross-sectional views of representative composites formed in accordance with the present invention.
Figure 4C:
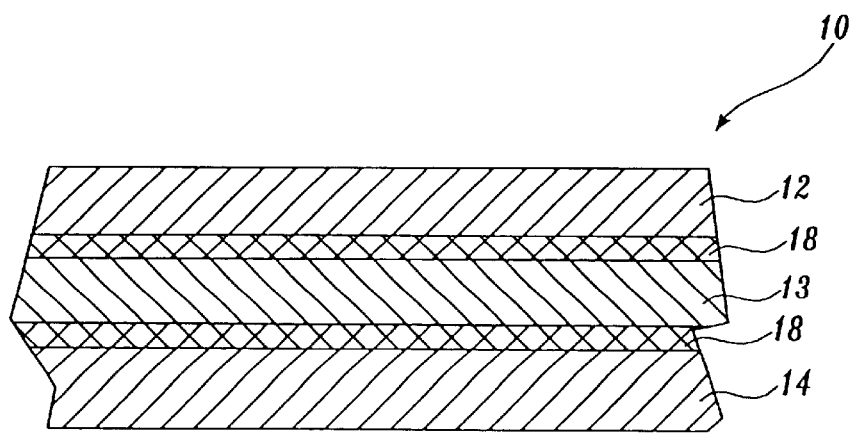
Figure 4D:
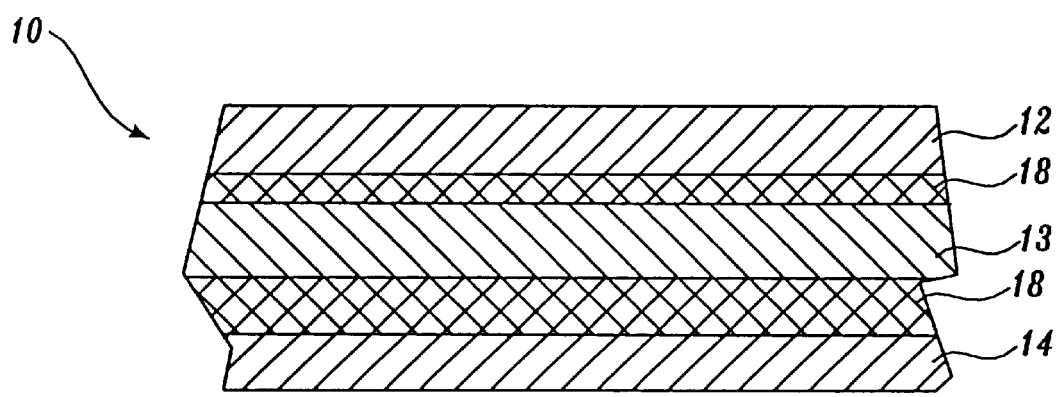

Referring to FIG. 4A, headbox 212 includes walls 222 and 224 and dividers 214a and 214b creating first chamber 226, second chamber 228, and third chamber 227. The length of dividers 214a and 214b can be varied such that the point at which furnishes introduced into chambers 226, 227 and 228 meet and commence mixing can be adjusted. The variances in the length of dividers 214a and 214b are depicted as dashed lines in FIG. 4A. In accordance with the present invention, the point at which furnishes meet and commence mixing in the headbox (e.g., the length of dividers) need not be the same. By adjusting the point at which furnishes meet, composites having individual strata and transitions zones having variable thickness within the composite can be provided. For example, a three-strata composite can have two transitions zones having the same thickness as shown in FIGS. 4B and 4C. Referring to FIGS. 4B and 4C, representative composites 10 have first stratum 12, second stratum 14, third stratum 13, and transition zones 18. The thicker transition zones 18 in FIG. 4B compared to the thinner transition zones 18 in FIG. 4C result from forming using the headbox of FIG. 4A using relatively shorter dividers 214a and 214b. Alternatively, as described above and illustrated in FIG. 4D, representative composite 10 can include transition zones 18 having different thicknesses.

Figure 5A:
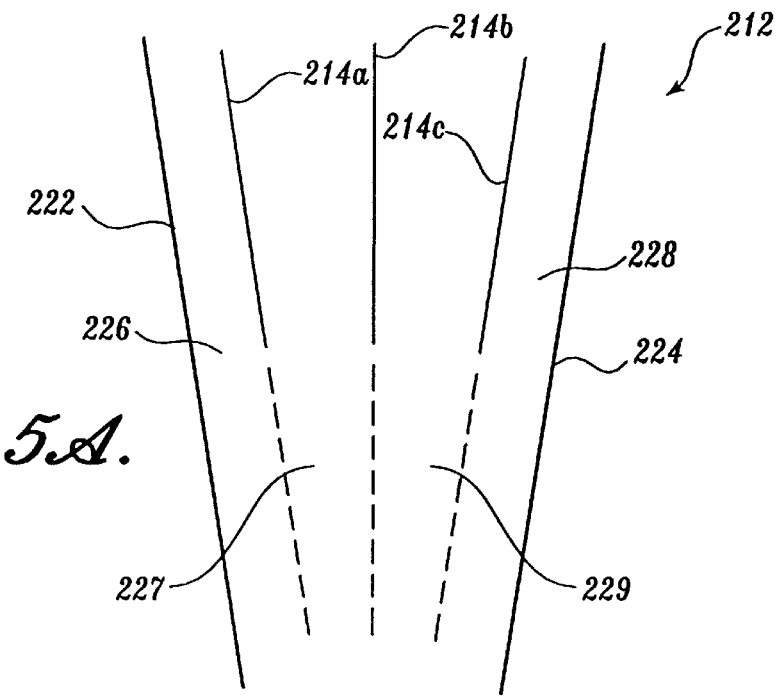
FIG. 5A is a diagram of a divided headbox for forming a representative composite according to the present invention.
Figure 5B:
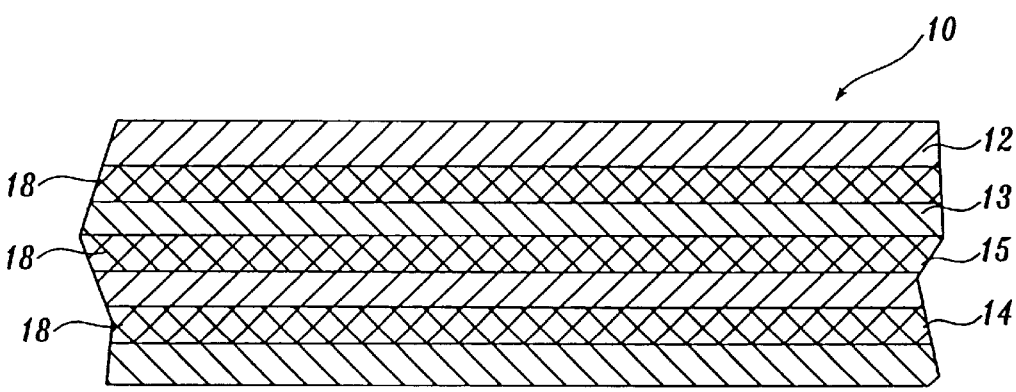
FIGS. 5B and 5C are cross-sectional views of representative composites formed in accordance with the present invention.
Figure 5C:
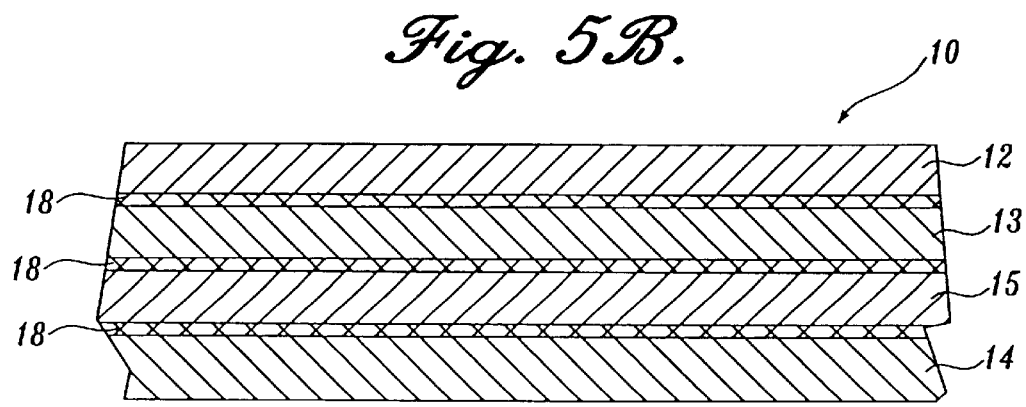

Referring to FIG. 5A, headbox 212 includes walls 222 and 224 and dividers 214a, 214b, and 214c, creating first chamber 226, second chamber 228, third chamber 227, and fourth chamber 229. The length of dividers 214a, 214b, and 214c can be varied such that the point at which furnishes introduced into chambers 226, 227, 228, and 229 meet and commence mixing can be adjusted. The variances in the length of dividers 214a, 214b, and 214c are depicted as dashed lines in FIG. 5A. As noted above, the point at which furnishes meet and commence mixing in the headbox (e.g., the length of dividers) need not be the same. Referring to FIGS. 5B and 5C, representative composites 10 have first stratum 12, second stratum 14, third stratum 13, fourth stratum 15, and transition zones 18. The thicker transition zones 18 in FIG. 5B compared to the thinner transition zones 18 in FIG. 5C result from forming using the headbox of FIG. 5A using relatively shorter dividers 214a, 214b, and 214c. Alternatively, as described above, representative composite 10 can include transition zones 18 having different thicknesses.

Figure 6A:
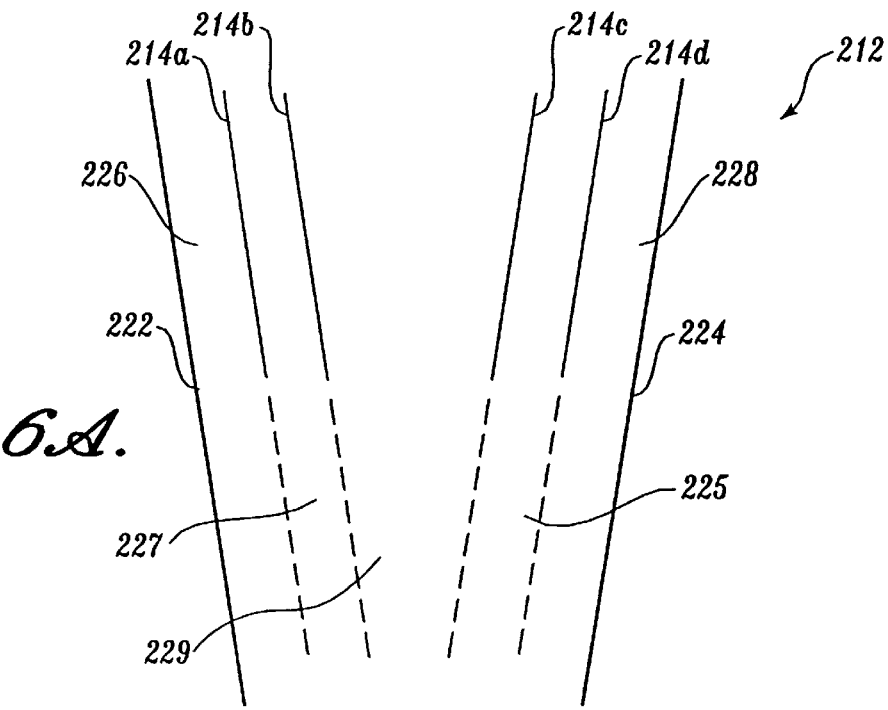
FIG. 6A is a diagram of a divided headbox for forming a representative composite according to the present invention.
Figure 6B:
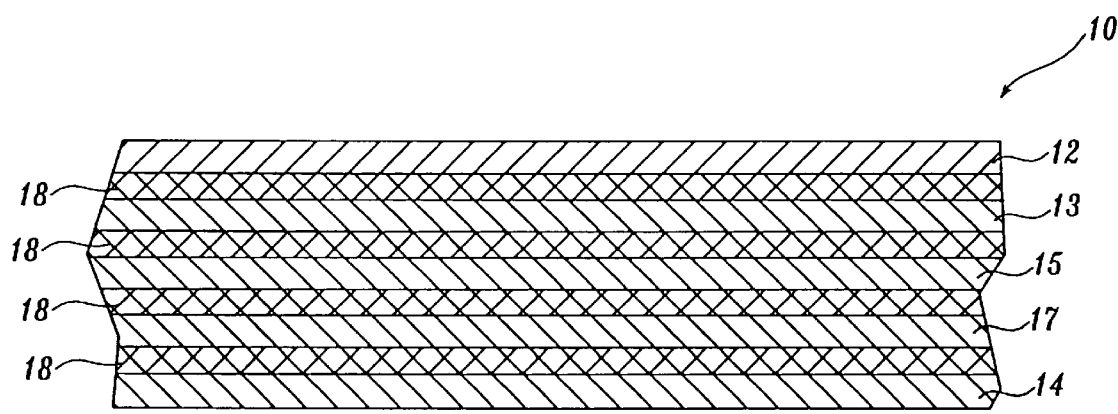
FIGS. 6B and 6C are cross-sectional views of representative composites formed in accordance with the present invention.
Figure 6C:
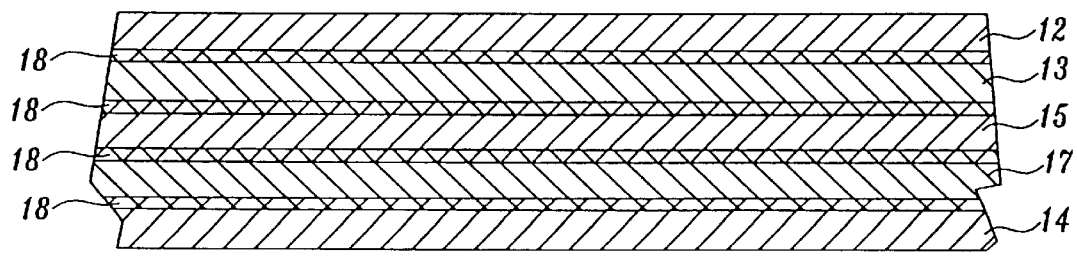

Referring to FIG. 6A, headbox 212 includes walls 222 and 224 and an dividers 214a, 214b, 214c, and 214d, creating first chamber 226, second chamber 228, third chamber 227, fourth chamber 229, and fifth chamber 225. The length of dividers 214a, 214b, 214c, and 214d can be varied such that the point at which furnishes introduced into chambers 225, 226, 227, 228, and 229 meet and commence mixing can be adjusted. The variances in the length of dividers 214a, 214b, 214c, and 214d are depicted as dashed lines in FIG. 6A. As noted above, the point at which furnishes meet and commence mixing in the headbox (e.g., the length of dividers) need not be the same. Referring to FIGS. 6B and 6C, representative composites 10 have first stratum 12, second stratum 14, third stratum 13, fourth stratum 15, fifth stratum 17, and transition zones 18. The thicker transition zones 18 in FIG. 6B compared to the thinner transition zones 18 in FIG. 6C result from forming using the headbox of FIG. 6A using relatively shorter dividers 214a, 214b, 214c, and 214d. Alternatively, as described above, representative composite 10 can include transition zones 18 having different thicknesses.

In one aspect, the present invention provides multistrata composites having multiple strata separated by transitions zones. The number and nature of each stratum of a particular composite of the invention can vary greatly depending on the end use of the composite. The number and nature of transitions zones in a particular composite can also be variable. Although representative composites of the invention described above include from two to five strata separated by one to four transitions zones, respectively, it will be appreciated that composites having additional strata and additional transition zones are within the scope of this invention.

The composites of the invention are fibrous composites that include two or more strata. The composites' component strata can vary greatly in composition depending on the desired end use of the composite. For example, a unitary composite having five strata can be provided where the first stratum includes the components such that the stratum serves as a liquid pervious topsheet; the second stratum includes components such that the stratum serves as an acquisition stratum for rapidly acquiring liquid; the third stratum includes components such that the stratum serves as a distribution layer for receiving liquid from the acquisition layer and distributing the liquid throughout the composites; the fourth stratum includes components such that the stratum serves as a storage layer for storing and retaining liquids acquired by the acquisition layer and distributed by the distribution layer; and the fifth stratum includes components such that the stratum serves as a liquid impervious backsheet. Alternatively, the composite of the invention can include fewer strata and can serve as a component or core having a specific functionality for an absorbent article.

A representative unitary composite exhibiting a relatively abrupt transition in material composition in the transition zone is illustrated in FIG. 7. The representative composite includes synthetic fibers, crosslinked cellulose fibers, superabsorbent polymer, and cellulosic fluff pulp. FIG. 7 illustrates the composition of the absorbent composite as a function of position (i.e., from the top to the bottom of the composite). FIG. 7 illustrates the transition zones, i.e., the overlap of compositions of the particular strata in the composite. Referring to FIG. 7, the top surface of the composite is composed exclusively of synthetic fibers. The bottom surface of the composite is composed of about 80 percent cellulosic fluff pulp and about 20 percent crosslinked cellulose fibers. At a position about one-third from the top of the composite, the composition of the composite is about 90 percent crosslinked cellulosic fibers and about 10 percent synthetic fibers. At a position about two-thirds from the top of the composite, the composite includes about 40 percent cellulosic fluff pulp, 45 percent superabsorbent polymer, and about 15 percent crosslinked cellulosic fibers. The transition zones between the uppermost synthetic fiber stratum and the adjacent crosslinked cellulosic fiber stratum is shown by the overlap composition occurring at about position 3.75. Similarly, the transition zone between the crosslinked cellulosic fiber stratum and the adjacent stratum including the combination of superabsorbent polymer and cellulosic fluff pulp is shown at about position 7.5. The transition zone between the crosslinked cellulosic fibers and the stratum that includes superabsorbent polymer and cellulosic fluff pulp also includes a small portion of synthetic fibers. As generally illustrated in FIG. 7, a unitary absorbent composite formed in accordance with the present invention is a multistrata composite in which the composition from one stratum to the next is a relatively continuous gradient.

Figure 8:
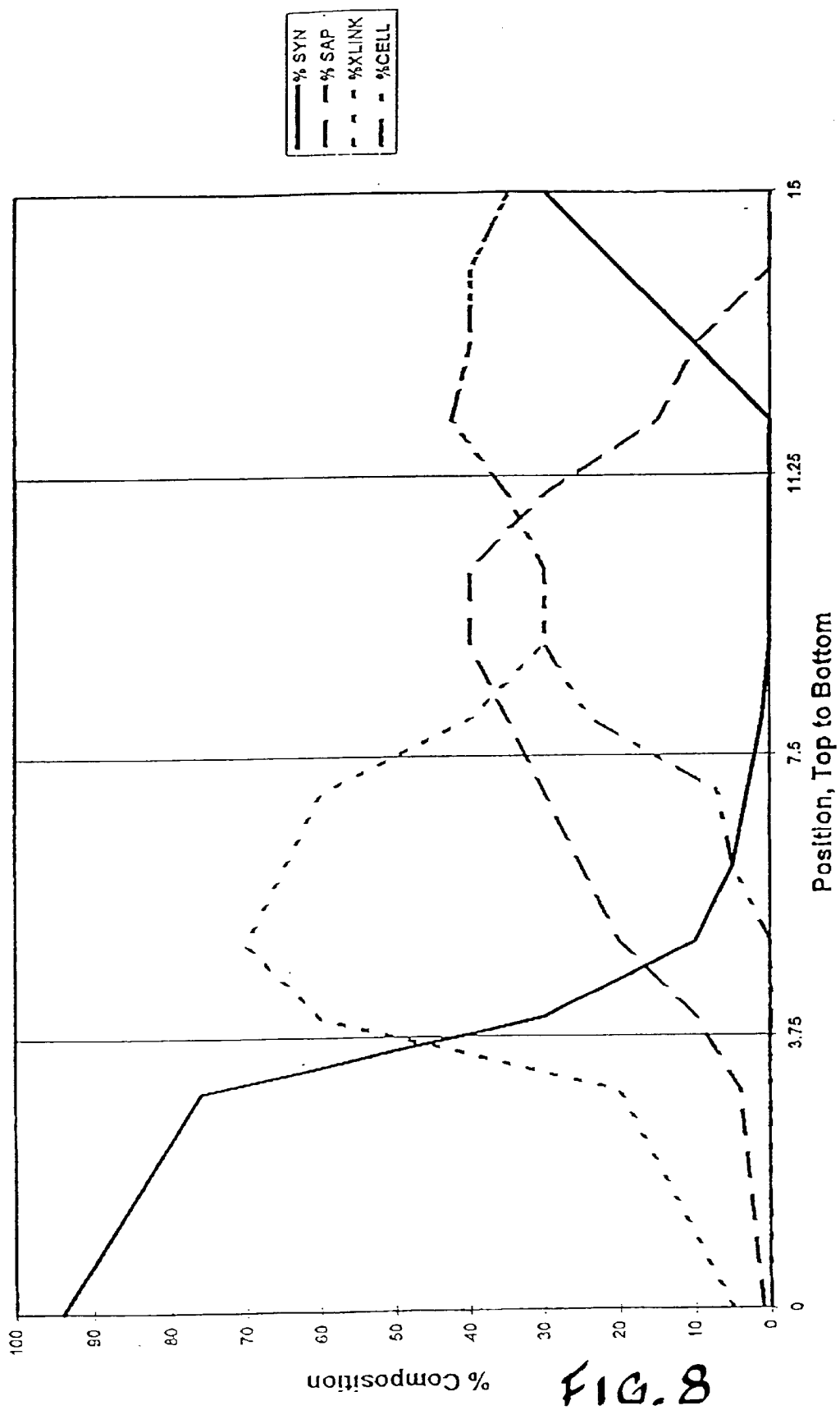
FIG. 8 is a diagram illustrating the composition of a representative composite formed in accordance with the present invention through the composite's thickness.

A representative absorbent composite exhibiting gradual transition zones between its strata is shown in FIG. 8, which illustrates the composition of the composite as a function of its thickness. Referring to FIGS. 7 and 8, the transition zones of the absorbent composite illustrated in FIG. 8 are broader and occur over a broader range of thickness of the composite as compared to the composite illustrated in FIG. 7. Referring to FIG. 8, the composition of the composite at its top surface is about 95 percent synthetic fibers, about 4 percent crosslinked cellulosic fibers, and about 1 percent superabsorbent polymer. At a position about one-third from the top of the composite, all of the components of the composite are present, i.e., about 60 percent crosslinked cellulosic fibers, about 30 percent superabsorbent polymer, and about 5 percent each of synthetic fibers and cellulosic fluff pulp.

The individual strata of the composites of the invention are formed from furnishes, typically fibrous furnishes, including materials specific for performance of the function desired by the particular stratum and the composite as a whole. Accordingly, the composites of the invention can include a variety of materials. In general, in addition to fibrous materials, such as cellulosic and synthetic fibers, the composites (i.e., composites' strata) can include absorbent material, such as superabsorbent polymers, and a binder for increasing the strength of the composite, as well as other additives commonly included in conventional absorbent composites.

Fibers are a principal component of the absorbent composite of the invention. Fibers suitable for use in the present invention are known to those skilled in the art and include any fiber from which an absorbent composite can be formed. Suitable fibers include natural and synthetic fibers. Combinations of fibers including combinations of synthetic and natural fibers, and treated and untreated fibers, can also be suitably used in the composite.

Generally, fibers are present in the composite in an amount from about 20 to about 100 weight percent, preferably from about 20 to about 80 weight percent, based on the total weight of the composite. In a preferred embodiment, the composite includes about 30 to about 60 percent by weight fibers.

The composite of the invention includes resilient fibers. As used herein, the term "resilient fiber" refers to a fiber present in the composite that imparts reticulation to the composite. Generally, resilient fibers provide the composite with bulk and resiliency. The incorporation of resilient fibers into the composite allows the composite to expand on absorption of liquid without structural integrity loss. Resilient fibers also impart softness to the composite. In addition, resilient fibers offer advantages in the composite's formation processes. Because of the porous and open structure resulting from wet composites that include resilient fibers, these composites drain water relatively easily and are therefore dewatered and dried more readily than wet composites that do not include resilient fibers. Preferably, the composite includes resilient fibers in an amount from about 10 to about 60 percent by weight, more preferably from about 20 to 50 percent by weight, based on the total weight of the composite.

Resilient fibers include cellulosic and synthetic fibers. Preferred resilient fibers include chemically stiffened fibers, anfractuous fibers, chemithermomechanical pulp (CTMP), and prehydrolyzed kraft pulp (PHKP).

The term "chemically stiffened fiber" refers to a fiber that has been stiffened by chemical means to increase fiber stiffness under dry and wet conditions. Fibers can be stiffened by the addition of chemical stiffening agents that can coat and/or impregnate the fibers. Stiffening agents, include the polymeric wet strength agents including resinous agents such as, for example, polyamide-epichlorohydrin and polyacrylamide resins described below. Fibers can also be stiffened by modifying fiber structure by, for example, chemical crosslinking. Preferably, the chemically stiffened fibers are intrafiber crosslinked cellulosic fibers.

Resilient fibers can include noncellulosic fibers including, for example, synthetic fibers such as polyolefin, polyamide, and polyester fibers. In a preferred embodiment, the resilient fibers include crosslinked cellulosic fibers.

As used herein, the term "anfractuous fiber" refers to a cellulosic fiber that has been chemically treated. Anfractuous fibers include, for example, fibers that have been treated with ammonia.

In addition to resilient fibers, the composite of the invention includes matrix fibers. As used herein, the term "matrix fiber" refers to a fiber that is capable of forming hydrogen bonds with other fibers. Matrix fibers are included in the composite to impart strength to the composite. Matrix fibers include cellulosic fibers such as wood pulp fibers, highly refined cellulosic fibers, and high surface area fibers such as expanded cellulose fibers. Other suitable cellulosic fibers include cotton linters, cotton fibers, and hemp fibers, among others. Preferably, the composite includes matrix fibers in an amount from about 10 to about 50 percent by weight, more preferably from about 15 to about 30 percent by weight, based on the total weight of the composite.

The composite of the present invention preferably includes a combination of resilient and matrix fibers. In one preferred embodiment, the composite includes resilient fibers in an amount from about 25 to about 50 percent by weight and matrix fibers in an amount from about 10 to about 40 percent by weight based on the total weight of the composite. In a more preferred embodiment, the composite includes from about 30 to about 45 percent by weight resilient fibers, preferably crosslinked cellulosic fibers, and from about 15 to about 30 percent by weight matrix fibers, preferably wood pulp fibers, based on the total weight of fibers in the composite. For representative composites formed by wet-laid and foam processes, the composite preferably includes about 45 percent by weight resilient fibers (e.g., crosslinked cellulosic fibers) and about 15 percent by weight matrix fibers.

Cellulosic fibers can be a basic component of the absorbent composite. Although available from other sources, cellulosic fibers are derived primarily from wood pulp. Suitable wood pulp fibers for use with the invention can be obtained from well-known chemical processes such as the kraft and sulfite processes, with or without subsequent bleaching. Pulp fibers can also be processed by thermomechanical, chemithermomechanical methods, or combinations thereof. The preferred pulp fiber is produced by chemical methods. Ground wood fibers, recycled or secondary wood pulp fibers, and bleached and unbleached wood pulp fibers can be used. Softwoods and hardwoods can be used. Details of the selection of wood pulp fibers are well-known to those skilled in the art. These fibers are commercially available from a number of companies, including Weyerhaeuser Company, the assignee of the present invention. For example, suitable cellulose fibers produced from southern pine that are usable with the present invention are available from Weyerhaeuser Company under the designations CF416, NF405, PL416, FR516, and NB416.

Suitable wood pulp fibers can also be pretreated prior to use with the present invention. This pretreatment may include physical treatment, such as subjecting the fibers to steam, or chemical treatment, for example, crosslinking the cellulose fibers using any one of a variety of crosslinking agents. Crosslinking increases fiber bulk and resiliency, and thereby can improve the fibers' absorbency. Generally, crosslinked fibers are twisted or crimped. The use of crosslinked fibers allows the composite to be more resilient, softer, bulkier, and to have enhanced wicking. Suitable crosslinked cellulose fibers produced from southern pine are available from Weyerhaeuser Company under the designation NHB416. Crosslinked cellulose fibers and methods for their preparation are disclosed in U.S. Pat. Nos. 5,437,418 and 5,225,047 issued to Graef et al., expressly incorporated herein by reference.

Crosslinked fibers can be prepared by treating fibers with a crosslinking agent. Suitable cellulose crosslinking agents include aldehyde and urea-based formaldehyde addition products. See, for example, U.S. Pat. Nos. 3,224,926; 3,241,533; 3,932,209; 4,035,147; 3,756,913; 4,689,118; 4,822,453; U.S. Pat. No. 3,440,135, issued to Chung; U.S. Pat. No. 4,935,022, issued to Lash et al.; U.S. Pat. No. 4,889,595, issued to Herron et al.; U.S. Pat. No. 3,819,470, issued to Shaw et al.; U.S. Pat. No. 3,658,613, issued to Steiger et al.; and U.S. Pat. No. 4,853,086, issued to Graef et al., all of which are expressly incorporated herein by reference in their entirety. Cellulose fibers have also been crosslinked by carboxylic acid crosslinking agents including polycarboxylic acids. U.S. Pat. Nos. 5,137,537; 5,183,707; and 5,190,563, describe the use of C2–C9 polycarboxylic acids that contain at least three carboxyl groups (e.g., citric acid and oxydisuccinic acid) as crosslining agents.

Suitable urea-based crosslinking agents include methylolated ureas, methylolated cyclic ureas, methylolated lower alkyl substituted cyclic ureas, methylolated dihydroxy cyclic ureas, dihydroxy cyclic ureas, and lower alkyl substituted cyclic ureas. Specific preferred urea-based crosslinking agents include dimethylol urea (DMU, bis[N-hydroxymethyl]urea), dimethylolethylene urea (DMEU, 1,3-dihydroxymethyl-2-imidazolidinone), dimethyloldihydroxyethylene urea (DMDHEU, 1,3-dihydroxymethyl-4,5-dihydroxy-2-imidazolidinone), dimethyldihydroxy urea (DMDHU), dihydroxyethylene urea (DHEU, 4,5-dihydroxy-2-imidazolidinone), and dimethyldihydroxyethylene urea (DMeDHEU, 4,5-dihydroxy-1,3-dimethyl-2-imidazolidinone).

Suitable polycarboxylic acid crosslinking agents include citric acid, tartaric acid, malic acid, succinic acid, glutaric acid, citraconic acid, itaconic acid, tartrate monosuccinic acid, and maleic acid. Other polycarboxylic acids crosslinking agents include polymeric polycarboxylic acids such as poly(acrylic acid), poly(methacrylic acid), poly(maleic acid), poly(methylvinylether-co-maleate) copolymer, poly(methylvinylether-co-itaconate) copolymer, copolymers of acrylic acid, and copolymers of maleic acid. The use of polymeric polycarboxylic acid crosslinking agents such as polyacrylic acid polymers, polymaleic acid polymers, copolymers of acrylic acid, and copolymers of maleic acid is described in U.S. patent application Ser. No. 08/989,697, filed Dec. 12, 1997, and assigned to Weyerhaeuser Company. Mixtures or blends of crosslinking agents may also be used.

The crosslinking agent can include a catalyst to accelerate the bonding reaction between the crosslinking agent and cellulose fiber. Suitable catalysts include acidic salts, such as ammonium chloride, ammonium sulfate, aluminum chloride, magnesium chloride, and alkali metal salts of phosphorous-containing acids.

Although not to be construed as a limitation, examples of pretreating fibers include the application of surfactants or other liquids which modify the surface chemistry of the fibers. Other pretreatments include incorporation of antimicrobials, pigments, dyes and densification or softening agents. Fibers pretreated with other chemicals, such as thermoplastic and thermosetting resins also may be used. Combinations of pretreatments also may be employed. Similar treatments can also be applied after the composite formation in post-treatment processes.

Cellulosic fibers treated with particle binders and/or densification/softness aids known in the art can also be employed in accordance with the present invention. The particle binders serve to attach other materials, such as cellulosic fiber superabsorbent polymers, as well as others, to the cellulosic fibers. Cellulosic fibers treated with suitable particle binders and/or densification/softness aids and the process for combining them with cellulose fibers are disclosed in the following U.S. patents: (1) U.S. Pat. No. 5,543,215, entitled "Polymeric Binders for Binding Particles to Fibers"; (2) U.S. Pat. No. 5,538,783, entitled "Non-Polymeric Organic Binders for Binding Particles to Fibers"; (3) U.S. Pat. No. 5,300,192, entitled "Wet Laid Fiber Sheet Manufacturing With Reactivatable Binders for Binding Particles to Binders"; (4) U.S. Pat. No. 5,352,480, entitled "Method for Binding Particles to Fibers Using Reactivatable Binders"; (5) U.S. Pat. No. 5,308,896, entitled "Particle Binders for High-Bulk Fibers"; (6) U.S. Pat. No. 5,589,256, entitled "Particle Binders that Enhance Fiber Densification"; (7) U.S. Pat. No. 5,672,418, entitled "Particle Binders"; (8) U.S. Pat. No. 5,607,759, entitled "Particle Binding to Fibers"; (9) U.S. Pat. No. 5,693,411, entitled "Binders for Binding Water Soluble Particles to Fibers"; (10) U.S. Pat. No. 5,547,745, entitled "Particle Binders"; (11) U.S. Pat. No. 5,641,561, entitled "Particle Binding to Fibers"; (12) U.S. Pat. No. 5,308,896, entitled "Particle Binders for High-Bulk Fibers"; (13) U.S. Pat. No. 5,498,478, entitled "Polyethylene Glycol as a Binder Material for Fibers"; (14) U.S. Pat. No. 5,609,727, entitled "Fibrous Product for Binding Particles"; (15) U.S. Pat. No. 5,571,618, entitled "Reactivatable Binders for Binding Particles to Fibers"; (16) U.S. Pat. No. 5,447,977, entitled "Particle Binders for High Bulk Fibers"; (17) U.S. Pat. No. 5,614,570, entitled "Absorbent Articles Containing Binder Carrying High Bulk Fibers; (18) U.S. Pat. No. 5,789,326, entitled "Binder Treated Fibers"; and (19) U.S. Pat. No. 5,611,885, entitled "Particle Binders"; all expressly incorporated herein by reference.

Modified cellulosic fibers useful in the invention include rayon and cellulose acetate fibers.

In addition to natural fibers, synthetic fibers including polymeric fibers, such as polyolefin, polyamide, polyester, polyvinyl alcohol, polyvinyl acetate fibers, can also be used in the absorbent composite of the present invention. Suitable synthetic fibers include, for example, polyethylene terephthalate, polyethylene, polypropylene, and nylon fibers. Other suitable synthetic fibers include those made from thermoplastic polymers, cellulosic and other fibers coated with thermoplastic polymers, and multicomponent fibers in which at least one of the components includes a thermoplastic polymer. Single and multicomponent fibers can be manufactured from polyester, polyethylene, polypropylene, and other conventional thermoplastic fibrous materials. Single and multicomponent fibers are commercially available. Suitable bicomponent fibers include Celbond® fibers available from. Hoechst-Celanese Company. The absorbent composite can also include combinations of natural and synthetic fibers. Synthetic fibers, including blends of natural and synthetic fibers, can be utilized in the composite's flutes and/or distribution zones.

In one preferred embodiment, the absorbent composite includes a combination of pulp fibers (e.g., Weyerhaeuser designation NB416), crosslinked cellulosic fibers (e.g., Weyerhaeuser designation NHB416), and synthetic fibers. In a preferred embodiment, the absorbent composite includes a combination of pulp fibers present in the composite in about 45 weight percent, crosslinked cellulosic fibers present in the composite in about 45 weight percent, and synthetic fibers present in the composite in about 10 percent by weight based on the total weight of fibers.

To enhance liquid absorption, acquisition, distribution, and storage, one of more strata of a composite of the invention can include absorbent material. As use herein, the term "absorbent material" refers to a material that absorbs liquid and that generally has an absorbent capacity greater than the cellulosic fibrous component of the composite. Preferably, the absorbent material is a water swellable, generally water insoluble polymeric material capable of absorbing at least about 5, desirably about 20, and preferably about 100 times or more its weight in saline (e.g., 0.9 percent saline). The absorbent material can be swellable in the dispersion medium utilized in the method for forming the composite. In one embodiment, the absorbent material is untreated and swellable in the dispersion medium. In another embodiment, the absorbent material is an absorbent material that is resistant to absorbing water during the composite formation process. Such absorbent materials that are resistant to absorption include coated and chemically modified absorbent materials.

The amount of absorbent material present in the composite can vary greatly depending on the composite's intended use. When the absorbent composite is used as a stand alone absorbent composite as in, for example, an absorbent toweling, the amount of absorbent material in the composite is comparative low (e.g., about 0.1 weight percent). The amount of absorbent material present in an absorbent article such as an absorbent core for an infant's diaper is considerably greater. In such a construct, the absorbent material is suitably present in the composite in an amount from about 10 to about 80 weight percent, preferably from about 30 to about 50 weight percent, based on the total weight of the composite. In preferred embodiments, the composite includes about 40 percent by weight absorbent material based on the total weight of the composite.

The absorbent material may include natural materials such as agar, pectin, and guar gum, and synthetic materials, such as synthetic hydrogel polymers. Synthetic hydrogel polymers include, for example, carboxymethyl cellulose, alkaline metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulphonic acid, polyacrylates, polyacrylamides, and polyvinyl pyridine among others. In a preferred embodiment, the absorbent material is a superabsorbent material. As used herein, a "superabsorbent material" refers to a polymeric material that is capable of absorbing large quantities of fluid by swelling and forming a hydrated gel (i.e., a hydrogel). In addition to absorbing large quantities of fluids, superabsorbent polymers can also retain significant amounts of bodily fluids under moderate pressure.

Superabsorbent polymers generally fall into three classes: starch graft copolymers, crosslinked carboxymethylcellulose derivatives, and modified hydrophilic polyacrylates. Examples of such absorbent polymers include hydrolyzed starch-acrylonitrile graft copolymers, neutralized starch-acrylic acid graft copolymers, saponified acrylic acid estervinyl acetate copolymers, hydrolyzed acrylonitrile copolymers or acrylamide copolymers, modified crosslinked polyvinyl alcohol, neutralized self-crosslinking polyacrylic acids, crosslinked polyacrylate salts, carboxylated cellulose, and neutralized crosslinked isobutylene-maleic anhydride copolymers.

Superabsorbent polymers are available commercially, for example, polyacrylates from Clariant of Portsmouth, Va. These superabsorbent polymers come in a variety of sizes, morphologies and absorbent properties (available from Clariant under trade designations such as IM 3500 and IM 3900). Other superabsorbent particles are marketed under the trademarks SANWET (supplied by Sanyo Kasei Kogyo Kabushiki Kaisha), and SXM77 (supplied by Stockhausen of Greensboro, N.C.). Other superabsorbent polymers are described in U.S. Pat. No. 4,160,059; U.S. Pat. No. 4,676,784; U.S. Pat. No. 4,673,402; U.S. Pat. No. 5,002,814; U.S. Pat. No. 5,057,166; U.S. Pat. No. 4,102,340; and U.S. Pat. No. 4,818,598, all expressly incorporated herein by reference. Products such as diapers that incorporate superabsorbent polymers are described in U.S. Pat. No. 3,699,103 and U.S. Pat. No. 3,670,731.

Suitable superabsorbent polymers useful in the absorbent composite of the present invention include superabsorbent polymer particles and superabsorbent polymer fibers.

In a preferred embodiment, the absorbent composite of the present invention includes a superabsorbent material that that swells relatively slowly for the purposes of composite manufacturing and yet swells at an acceptable rate so as not to adversely affect the absorbent characteristics of the composite or any construct containing the composite.

In one embodiment, the present invention provides a composite having absorbent material present in the composite in a concentration gradient. As used herein, the term "concentration gradient" refers to a gradient in the concentration of absorbent material in the fibrous composite with respect to a particular dimension (i.e., thickness, width, and length) of the composite. An absorbent material concentration gradient is formed through selective distribution of the material into the composite. For example, as described below, introduction of the absorbent material into the composite can be accomplished with significant fiber mixing and an accompanying loss of an absorbent material concentration gradient. Alternatively, the absorbent material can be introduced into the composite without significant fiber mixing resulting in the formation of a relatively greater concentration gradient. The composite's concentration gradient can be present in either the z-direction (i.e., the thickness of the composite), the x-direction (i.e., across the width of the composite, the cross-machine direction), the y-direction (i.e., along the length of the composite, the machine direction) or combinations of the x-, y- and z-directions. Concentration gradients of absorbent material are contemplated to increase liquid wicking and further to reduce the potential for gel blocking.

Increased wet and dry strength of the unitary composite of the present invention can be accomplished through the incorporation of a binder. Alternatively, for composites that do not include a binder, composite integrity can be achieved through densification.

As noted above, the composites of the invention can include a binder. Suitable binders include, but are not limited to, cellulosic and synthetic fibrous materials, bonding agents, soluble bonding mediums, and wet strength agents as described below. In one preferred embodiment, the binder includes bicomponent binding fibers, such as Celbond® (Hoechst Celanese) and D-271P® (DuPont). In another preferred embodiment, the binder includes a soluble binding medium, more preferably cellulose acetate used in combination with the solvent triacetin and/or triethyl citrate.

As used herein, the term "binder" refers to a system that is effective in mechanically intertwining or bonding the materials within a first stratum, or bonding the materials of a first stratum to a second stratum. In one embodiment of the present invention, all strata include a binder. Suitable binders can include, but are not limited to, bonding agents such as thermoplastic and thermosetting materials, soluble bonding mediums used in combination with solvents, and wet strength agents. Alternatively, integral commingling and intimate contact between the composite's strata can be achieved through mechanical processes including, for example, hydroentanglement, embossing, tenderizing, and needling processes, among others.

Bonding agents useful in the binder in accordance with the present invention are those materials that (a) are capable of being combined with and dispersed throughout a web of fibers, (b) when activated, are capable of coating or otherwise adhering to the fibers or forming a binding matrix, and (c) when deactivated, are capable of binding at least some of the fibers together. The use of bonding agents with cellulose fiber webs is disclosed in U.S. patent application Ser. No. 08/337,642, filed Nov. 10, 1994, entitled "Densified Cellulose Fiber Pads and Methods of Making the Same," expressly incorporated herein by reference.

Suitable bonding agents include thermoplastic materials that are activated by melting at temperatures above room temperature. When these materials are melted, they will coat at least portions of the cellulose fibers with which they are combined. When the thermoplastic bonding agents are deactivated by cooling to a temperature below their melt point, and preferably no lower than room temperature, the bonding agent will, upon solidifying from the melted state, cause the cellulose fibers to be bound in a matrix.

Thermoplastic materials are the preferred binders, and can be combined with the fibers in the form of particles, emulsions, or as fibers. Suitable fibers can include those made from thermoplastic polymers, cellulosic or other fibers coated with thermoplastic polymers, and multicomponent fibers in which at least one of the components of the fiber comprises a thermoplastic polymer. Single and multicomponent fibers are manufactured from polyester, polyethylene, polypropylene, and other conventional thermoplastic fiber materials. The same thermoplastics can be used in particulate or emulsion form. Many single-component fibers are readily commercially available. Suitable multicomponent fibers include Celbond® fibers available from Hoechst Celanese Company. A preferred crimped polymer-based binder fiber is Hoechst. Celanese copolyolefin bicomponent fiber, commercially available under the tradename CELBOND® from Hoechst Celanese Corporation, type 255, lot 33865A, having a detex of about 3.3, a denier of about 3.0, and a fiber length of about 6.4 mm. Suitable coated fibers can include cellulose fibers coated with latex or other thermoplastics, as disclosed in U.S. Pat. No. 5,230,959, issued Jul. 27, 1993, to Young et al., and U.S. Pat. No. 5,064,689, issued Nov. 12, 1991, to Young et al. The thermoplastic fibers are preferably combined with the cellulose fibers before or during the forming process. When used in particulate or emulsion form, the thermoplastics can be combined with the cellulose fibers before, during, or after the forming process.

Other suitable thermoplastic bonding agents include ethylene vinyl alcohol, polyvinyl acetate, acrylics, polyvinyl acetate acrylate, polyvinyl dichloride, ethylene vinyl acetate, ethylene vinyl chloride, polyvinyl chloride, styrene, styrene acrylate, styrene butadiene, styrene acrylonitrile, butadiene acrylonitrile, acrylonitrile butadiene styrene, ethylene acrylic acid, urethanes, polycarbonate, polyphenylene oxide, and polyimides.

Thermosetting materials also serve as excellent bonding agents for the present invention. Typical thermosetting materials are activated by heating to elevated temperatures at which crosslinking occurs. Alternatively, a resin can be activated by combining it with a suitable crosslinking catalyst before or after it has been applied to the cellulosic fiber. Thermosetting resins can be deactivated by allowing the crosslinking process to run to completion or by cooling to room temperature, at which point crosslinking ceases. When crosslinked, it is believed that the thermosetting materials form a matrix to bond the cellulose fibers. It is contemplated that other types of bonding agents can also be employed, for example, those that are activated by contact with steam, moisture, microwave energy, and other conventional means of activation.

Thermosetting bonding agents suitable for the present invention include phenolic resins, polyvinyl acetates, urea formaldehyde, melamine formaldehyde, and acrylics. Other thermosetting bonding agents include epoxy, phenolic, bismaleimide, polyimide, melamine formaldehyde, polyester, urethanes, and urea.

These bonding agents are normally combined with the fibers in the form of an aqueous emulsion. They can be combined with the fibers during the laying process. Alternatively, they can be sprayed onto a loose web after it has been formed.

As noted above, the binder utilized in accordance with the present invention can also be a soluble bonding medium that can be incorporated with the pulped cellulosic fibers, either in fiber form, or as particles or granules. If desired, the bonding medium can also be coated onto solvent-insoluble fibers, such as cellulosic fibers, which can then be distributed throughout the matrix of fibers making up each of the strata of the present invention. It is presently preferred that the bonding medium comprise a fiber and be mixed with the components of each stratum prior to the formation of the absorbent. The use of soluble bonding mediums with cellulose fiber webs is disclosed in U.S. Pat. No. 5,837,627, entitled "Fibrous Web Having Improved Strength and Method of Making the Same," expressly incorporated herein by reference.

The solvents employed in accordance with the present invention must of course be capable of partially solubilizing the bonding medium as described above. The solvents must be able to partially dissipate or migrate from the surface of the bonding medium to allow the bonding medium to resolidify after partial solubilization. Nonvolatile solvents may be dissipated in most part by absorption into the bonding medium. It is preferred that the solvent be of limited volatility, so that little or no solvent will be lost to the atmosphere. By limited volatility it is meant that the solvent has a vapor pressure of 29 kPa or less at 25° C. Using a solvent of limited volatility may mitigate precautions usually necessary to control volatiles, and reduces the amount of solvent required to partially solubilize the bonding medium. In addition, use of solvents of limited volatility may eliminate the attendant processing problems encountered with volatile solvents, many of which are flammable and must be handled with care. The use of solvents of limited volatility may also reduce environmental problems.

Furthermore, it is desirable for solvents to be nontoxic and capable of being dissipated from the surface of the bonding medium without adversely affecting the overall strength of the bonding medium.

Preferred bonding mediums and solvents of limited volatility are listed in the table set forth below.

| Bonding Medium | Solvent |
| --- | --- |
| cellulose acetate | triacetin |
| | propane diol diacetate |
| | propane diol dipropionate |
| | propane diol dibutyrate |
| | triethyl citrate |
| | dimethyl phthalate |
| | dibutyl phthalate |
| cellulose nitrate | triacetin |
| cellulose butyrate | triacetin |
| vinyl chloride/vinyl acetate copolymer | triacetin |
| cellulose fibers coated with polyvinyl acetate | triacetin |

Of the several bonding mediums listed, cellulose acetate is the most preferred. During manufacture of cellulose acetate fibers, a finish is usually applied to the fibers. Many times this finish is in the form of an oil. The presence of the finish sometimes detracts from the performance of a bonding medium. The presence of a finish may adversely affect the development as well as the strength of the bonds. It has been found that, when the bonding fibers are as straight as possible, as opposed to curled or kinked, they provide more contact points with the cellulosic fibers, and thus the final web will develop better strength. Similarly, when the bonding fibers are as long as is reasonably possible, the strength of the final web is increased. In addition to the foregoing, cellulose ethers and other cellulose esters may also be used as bonding medium. Acetylated pulp fibers may also be used as bonding medium and may be substituted with any number of acetyl groups. A preferred degree of substitution (D.S.) would be 2 to 3, and a most preferred D.S. would be 2.4.

The solvents used in combination with the bonding medium can be added in varying amounts. Strength is adversely affected if too little or too much solvent is added. At a cellulose acetate/pulp weight ratio of 10:90, it has been found that the solvents, and particularly triacetin, provide good strength when added in amounts ranging from 6% to 17%, and most preferably in the range of 9% to 14%, based on the weight of pulp fiber present.

The preferred forms of the solvents propane diol diacetate, dipropionate, and dibutyrate are the 1, 2 and 1, 3 forms. Other suitable solvents that work in accordance with present invention are butyl phthalyl butyl glycolate, N-cyclohexyl-p-toluenesulfonamide, diamyl phthalate, dibutyl phthalate, dibutyl succinate, dibutyl tartrate, diethylene glycol dipropionate, di-(2-ethoxyethyl) adipate, di-(2-ethoxyethyl) phthalate, diethyl adipate, diethyl phthalate, diethyl succinate, diethyl tartrate, di-(2-methoxyethyl) adipate, di-(2-methoxyethyl) phthalate, dimethyl phthalate, dipropyl phthalate, ethyl o-benzoylbenzoate, ethyl phthalyl ethyl glycolate, ethylene glycol diacetate, ethylene glycol dibutyrate, ethylene glycol dipropionate, methyl o-benzoylbenzoate, methyl phthalyl ethyl glycolate, N-o and p-tolylethylsulfonamide, o-tolyl p-toluenesulfonate, tributyl citrate, tributyl phosphate, tributyrin, triethylene glycol diacetate, triethylene glycol dibutyrate, triethylene glycol dipropionate, and tripropionin.

The binder useful in the absorbent composite of the invention can also include polymeric agents that can coat or impregnate cellulosic fibers. These wet strength agents provide increased strength to the absorbent composite and enhance the composites wet integrity. In addition to increasing the composites wet strength, the wet strength agent can assist in binding the absorbent material, for example, superabsorbent material, in the composite's fibrous matrix.

Suitable wet strength agents include cationic modified starch having nitrogen-containing groups (e.g., amino groups) such as those available from National Starch and Chemical Corp., Bridgewater, N.J.; latex; wet strength resins such as polyamide-epichlorohydrin resin (e.g., Kymene® 557LX, Hercules, Inc., Wilmington, Del.), polyacrylamide resin (described, for example, in U.S. Pat. No. 3,556,932 issued Jan. 19, 1971 to Coscia et al.; also, for example, the commercially available polyacrylamide marketed by American Cyanamid Co., Stanford, Conn., under the trade name Parez™ 631 NC); urea formaldehyde and melamine formaldehyde resins, and polyethylenimnine resins. A general discussion on wet strength resins utilized in the paper field, and generally applicable in the present invention, can be found in TAPPI monograph series No. 29, "Wet Strength in Paper and Paperboard", Technical Association of the Pulp and Paper Industry (New York, 1965).

Generally, the wet strength agent is present in the composition in an amount from about 0.01 to about 2 weight percent, preferably from about 0.1 to about 1 weight percent, and more preferably from about 0.3 to about 0.7 weight percent, based on the total weight of the composite. In a preferred embodiment, the wet strength agent useful in the composite of the present invention is a polyamide-epichlorohydrin resin such as commercially available from Hercules, Inc. under the designation Kymene®. The wet and dry tensile strength of an absorbent composite formed in accordance with the present invention will generally increase with an increasing the amount of wet strength agent.

Other binders could also include the use of scrim and/or continuous fiber filaments.

Additives can also be incorporated into the unitary composite formed in accordance with the present invention during absorbent formation. The advantage of incorporating the additives during the absorbent formation is that they will also be attached to the absorbent matrix. This provides a significant advantage in that the additives can be dispersed and retained throughout the matrix where desired. For example, the additives may be evenly dispersed and retained throughout the matrix. Additives that can be incorporated into the matrix include absorbent capacity enhancing materials such as superabsorbent polymers, adsorbents such as clays, zeolites, and activated carbon, brighteners such as titanium oxide, and odor absorbents such as sodium bicarbonate.

The composites of the present invention generally have a basis weight from about 50 to about 1000 $g/m^2$, and preferably from about 200 to about 800 $g/m^2$. In a more preferred embodiment, the absorbent composites have a basis weight from about 300 to about 600 $g/m^2$. The basis weight of any composite can be varied and will depend on its intended use. When the composite's intended use is as a storage layer, the composite preferably has a basis weight greater than about 300 $g/m^2$. For use as a liquid management layer, the composite preferably has a basis weight from about 100 to about 400 $g/m^2$.

The absorbent composite generally has an average density (in the cross-machine direction) of from about 0.03 to about 0.8 $g/cm^3$, preferably from about 0.04 to about 0.3 $g/cm^3$.

In one embodiment, the absorbent composite is a densified composite. Densification methods useful in producing the densified composites of the present invention are well known to those in the art. See, for example, U.S. Pat. No. 5,547,541 and patent application Ser. No. 08/859,743, filed May 21, 1997, entitled "Softened Fibers and Methods of Softening Fibers," assigned to Weyerhaeuser Company, both expressly incorporated herein by reference. Post dryer densified absorbent composites of this invention generally have a density from about 0.1 to about 0.5 $g/cm^3$, and preferably about 0.15 $g/cm^3$. Predryer densification can also be employed. Preferably, the absorbent composite is densified by either a heated or room temperature calender roll method. See, for example, U.S. Pat. Nos. 5,252,275 and 5,324,575, both expressly incorporated herein by reference.

The compositions of representative unitary composites formed in accordance with the present invention are summarized in Table 1 below. In the table, in addition to the type and amount of fibers in each stratum, the basis weight (BW in $g/m^2$) for each stratum is indicated. As used in the table, "Top" refers to the composite's upper stratum and "Bottom" refers to the composite's lower stratum, "PET" refers to polyethylene terephthalate fibers, "CPine" refers to Columbus Pine commercially available from Weyerhaeuser Company, and "XL" refers to crosslinked cellulosic fibers.

TABLE 1

Compositions of Representative Unitary Composites.

| Composite | BW Top/Bottom | PET Top | Binder Top/Bottom | Pulp Bottom | Ratio (pulp) Bottom | Tri Strata Bottom | PET Type/Denier |
|---|---|---|---|---|---|---|---|
| 1 | 40/100 | 80 | 20/10 | CPine/XL | 70/20 | | T224/15 |
| 2 | 40/160 | 80 | 20/10 | CPine/XL | 70/20 | | T224/15 |
| 3 | 20/30 | 80 | 20/10 | NB416/NHB416 | 70/20 | | T224/15 |
| 4 | 20/30 | 80 | 20/10 | NB416/NHB416 | 0/90 | | T224/15 |
| 5 | 20/180 | 80 | 20/10 | NB416/NHB416 | 70/20 | | T224/15 |
| 6 | 20/180 | 80 | 20/10 | NB416/NHB416 | 0/90 | | T224/15 |
| 7 | 25/50 | 80 | 20/20 | NB416/XL | 0/80 | | T224/15 |
| 8 | 25/50 | 80 | 20/20 | NB416/XL | 0/80 | | T224/15 |
| 9 | 25/75/100 | 80 | 20/20/20 | NB416/XL | 0/80 | 40/40 | T224/15 |
| 10 | 20/30 | 80 | 20/20 | NB416/NHB416 | 80/0 | | T303/4.75 |
| 11 | 10/40 | 90 | 10/10 | NB416/NHB416 | 90/0 | | T303/4.75 |
| 12 | 20/30 | 70/20 | 10/10 | NB416/NHB416 | 90/0 | | T303/4.75 |
| 13 | 20/30 | 80 | 20/10 | NB416/NHB416 | 70/20 | | |

TABLE 1-continued

Compositions of Representative Unitary Composites.

| Composite | BW Top/Bottom | PET Top | Binder Top/Bottom | Pulp Bottom | Ratio (pulp) Bottom | Tri Strata Bottom | PET Type/Denier |
|---|---|---|---|---|---|---|---|
| 14 | 20/30 | 80 | 20/10 | NB416/XL | 90/0 | | |
| 15 | 20/80 | 80 | 20/10 | NB416/XL | 70/20 | | |
| 16 | 40/160 | 90 | 10/10 | CPine | 90/0 | | |
| 17 | 20/180 | 80 | 20/10 | CPine/XL | 70/20 | | |
| 18 | 25/175 | 80 | 20/20 | CPine/XL | 0/80 | | |
| 19 | 40/180 | 80 | 20/10 | CPine/XL | 70/20 | | |
| 20 | 40/30 | 90 | 10/20 | NB416/NHB416 | 80/10 | | |
| 21 | 40/180 | 90 | 10/20 | NB416/NHB416 | 80/0 | | |
| 22 | 20/130 | 80 | 20/10 | NB416/NHB416 | 70/20 | | |
| 23 | 40/160 | 80 | 20/10 | NB416/NHB416 | 70/20 | | |
| 24 | 40/100 | 80 | 20/10 | CPine/XL | 70/20 | | T224/15 |

TABLE 2

Compositions of Representative Unitary Composites.

| Composite | BW Top/Bottom | PET Top | Binder Top/Bottom | Pulp Bottom | Ratio (pulp) Bottom | Density |
|---|---|---|---|---|---|---|
| 1 | 185 | — | 10 | NB416/NHB416 | | 0.165 |
| 2 | 206 | — | 10 | NB416/NHB416 | | 0.161 |
| 3 | 200 | — | 10 | NB416/NHB416 | | 0.149 |
| 4 | 198 | — | 10 | NB416/NHB416 | | 0.102 |

In another aspect of the present invention, methods for forming the unitary composite are provided. The absorbent composite of the present invention can be formed by wet-laid and foam-forming processes. These general methodologies are known to those of skill in the pulp processing art.

A representative example of a wet-laid process is described in U.S. Pat. No. 5,300,192, issued Apr. 5, 1994, entitled "Wet-Laid Fiber Sheet Manufacturing with Reactivatable Binders for Binding Particles to Fibers", expressly incorporated herein by reference. Wet-laid processes are also described in standard texts, such as Casey, Pulp and Paper, 2nd edition, 1960, Volume II, Chapter VIII—Sheet Formation. Representative foam processes useful in forming the composite of the present invention are known in the art and include those described in U.S. Pat. Nos. 3,716,449; 3,839,142; 3,871,952; 3,937,273; 3,938,782; 3,947,315; 4,166,090; 4,257,754; and 5,215,627, assigned to Wiggins Teape and related to the formation of fibrous materials from foamed aqueous fiber suspensions, and "The Use of an Aqueous Foam as a Fiber-Suspending Medium in Quality Papermaking," Foams, Proceedings of a Symposium organized by the Society of Chemical Industry, Colloid and Surface Chemistry Group, R. J. Akers, Ed., Academic Press, 1976, which describes the Radfoam process, all expressly incorporated herein by reference.

For composites of the invention that include absorbent material, the absorbent material is incorporated into the composite during the composite formation. Generally, the method for forming such an absorbent composite includes depositing absorbent material into a fibrous web, and then drying the web, as necessary, to provide the composite of the invention.

In a wet-laid method, absorbent material is preferably applied into a fibrous slurry that has been deposited onto a foraminous support (i.e., a forming wire). In the method, absorbent material is injected into an at least partially dewatered fibrous web formed by depositing a fibrous slurry onto a forming wire. The fibrous slurry preferably includes fibers and wet strength agent in a dispersion medium (e.g., a primarily aqueous medium such as water). The absorbent material can be introduced into the fibrous web as a dry particle or, preferably, as a liquid suspension in an aqueous medium, preferably chilled (e.g., 34–40° F.) water. The absorbent material is generally injected into the partially dewatered fibrous web immediately after the slurry's deposition onto the forming wire. The absorbent material is preferably deposited into the partially dewatered fibrous web (i.e., before dewatering of the web is completed and during the formation of the wet composite where the consistency of the web is increased relative to the slurry and, in any event, prior to the drying stage). After depositing the absorbent material into the partially dewatered fibrous web, the web containing fibers and absorbent material is subjected to further removal of at least a portion of the dispersion medium and water, preferably by vacuum, to provide a wet composite. The wet composite is then dried to provide the absorbent composite.

Alternatively, the absorbent material can be combined with other materials, such as cellulosic materials, in a fibrous furnish and introduced into a multichannel headbox as described above.

It is desirable to inhibit liquid absorption by the absorbent material during the web formation process. To inhibit liquid absorption, absorbent material can be added to the at least partially dewatered web as an aqueous suspension in chilled water having a temperature in the range from about 0–5° C., preferably from about 0.3° C.; and more preferably about 1° C. Alternatively, the absorbent material can be cooled to below 0° C., by placement or storage in a conventional freezer, and then forming a suspension in water, preferably chilled water, immediately prior to web formation. Limiting the period of time that the absorbent material is in contact with liquid during the forming process also has a positive effect on limiting absorbent material liquid absorption. For embodiments of the composite prepared by this method, the absorbent material suspension is preferably added to the at least partially dewatered fibrous web within about 10 seconds, and more preferably within about 5 seconds after preparing the suspension.

By limiting the liquid absorption by the absorbent material during the formation process, web drying energy and/or time, and the consequent associated expense can be greatly reduced. This advantage can result in web formation processes that are more cost effective and can represent significant savings for consumer absorbent products such as diapers, feminine care products, and adult incontinence products.

In one embodiment, the absorbent composite of the present invention can include bands of absorbent material that are spaced laterally across the composite's width and that extend longitudinally along the composite's length in the machine direction of the composite. These bands can be formed within a stratum of the composite of the invention. Such a configuration of bands can be achieved by various methods including injecting absorbent material into the fibrous web, which has been at least partially dewatered, through openings or nozzles spaced laterally across the width of the web. The nozzles are connected to an absorbent material supply. The nozzles can be positioned in various configurations and have orifices of varying size to provide bands having various configurations including, for example, various widths. The absorbent material is preferably deposited as a suspension in chilled water. For aqueous suspensions, the absorbent material is injected as a stream or jet into the partially dewatered fibrous web. Injection of the stream can result in significant mixing of the absorbent material and the fibers of the web. The degree of mixing can be controlled by several factors including stream velocity, web velocity, angle of injection, and position of injection relative to the deposition of fibrous slurry on the support, among others. Generally, the closer the absorbent material injection to the point at which dewatering of the fibrous web commences, the greater the mixing of absorbent material and fibers. Also, the greater the mixing of absorbent material and fibers, the lesser the resulting concentration gradient of absorbent material in the composite.

Figure 32A:
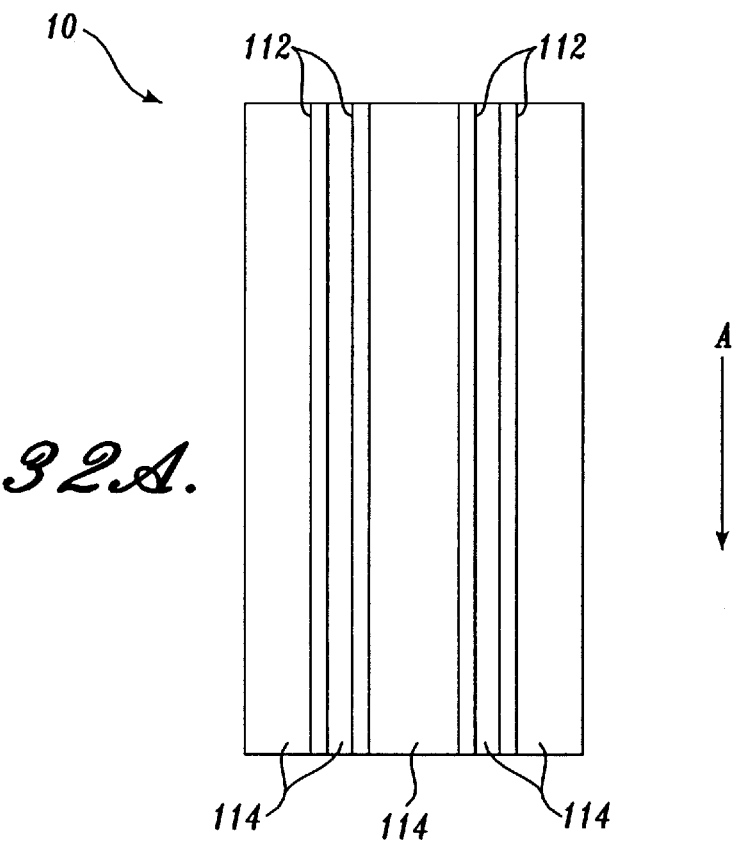
FIGS. 32A and 32B are schematic illustrations of representative strata containing absorbent material-enriched regions formed in accordance with the present invention.
Figure 32B:
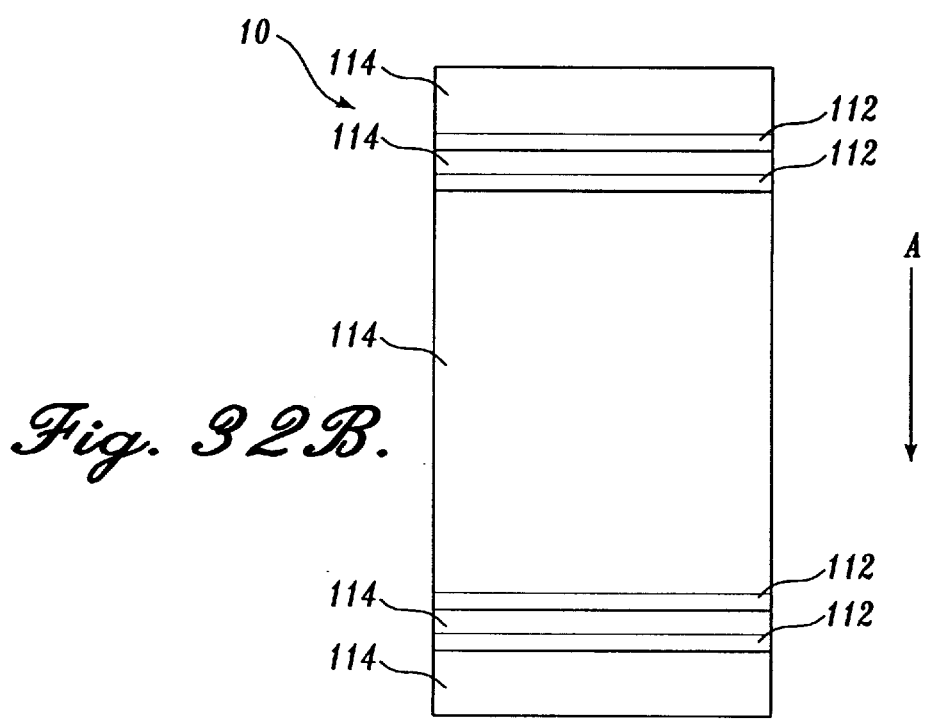

Alternatively, the composite can include a stratum having bands of absorbent material that run in the cross-machine direction of the web. For these composites, these bands can be positioned at opposite ends of the composite (e.g., a pair of bands at each end) with each band extending across the composite's width. When the composite is in its intended use position, the bands are located away from the crotch area of the wearer (i.e., away from the site of liquid insult). In such a composite, liquid is wicked away from the site of insult and retained in the bands positioned near the wearer's waist. Such a configuration draws liquid away from the insult site and provides for reduced rewet, which would be expected to increase skin health. Referring to FIGS. 32A and 32B, representative stratum 10 includes absorbent material enriched regions 112 and fibrous regions 114. In FIG. 32A, regions 112 run in the stratum's machine direction (direction A), and in FIG. 32B, regions 112 run in the cross-machine direction.

Because the bands of absorbent material can be formed in the composite by deposition or injection through individual nozzles, the nature and characteristics of the bands that are ultimately formed in the composite can be controlled. For example, the outermost bands can contain absorbent material in relatively greater amounts compared to the inner flutes. Such a composite can be formed by depositing greater concentrations of absorbent material, depositing absorbent material at a greater rate, or utilizing nozzles having larger diameter orifices for the outermost positions. As noted above, absorbent materials having different absorptive and retentive capacities can be selectively deposited in the bands.

The deposition of individual bands also allows for the formation of bands that can include materials in addition to absorbent material. For example, additional fibers can also be introduced into the deposited slurry through the use of these nozzles. Consequently, bands having additional fibers, including fibers different from the deposited fibrous slurry, can be incorporated into the composite. In one preferred embodiment, the absorbent composite includes bands of absorbent material that further include additional fibers such as, for example, hardwood fibers and/or synthetic fibers. The use of different fibers can be used to form bands having, for example, higher relative basis weights; greater bulk and softness; increased wicking; and increased rewet performance. Thus, the composite's bands can be formed from completely different components compared to the base composite (i.e., the initially deposited fibrous slurry).

The composite's absorbent material enriched regions can be stabilized to enhance the structural integrity of the band. Band integrity can be enhanced by depositing, in addition to absorbent material, a wet strength agent (e.g., Kymene®) and/or fibrous materials including, for example, microfibrillated cellulose and fibrous superabsorbent materials. Fibrous superabsorbent materials are described in U.S. Pat. No. 5,607,550, expressly incorporated herein by reference.

The advantage of versatility allows for the design and formation of various banded unitary absorbent composites. For example, base strata can be designed for strength and wicking, while the deposited bands can be designed to maximize swelling and absorbent capacity and to minimize rewet. More specifically, for an absorbent composite that maximizes absorbent capacity, strength, and total material utilization, the base strata can include a mixture of southern pine fibers, eucalyptus fibers, crosslinked fibers and wet strength agent, and the bands can include a mixture of absorbent material and crosslinked cellulosic fibers or other fibers. For a composite having increased capacity and enhanced wicking to the absorbent material, the base strata can include a mixture of southern pine fibers, eucalyptus fibers, and wet strength agent, and the bands can include a mixture of absorbent material, crosslinked cellulosic fibers, and microfibrillated cellulose. Another preferred absorbent composite includes a base strata composed of a refined mixture of crosslinked cellulosic fibers and eucalyptus fibers, and includes bands composed of a mixture of absorbent material and unrefined crosslinked fibers. To reduce rewet, synthetic fibers (e.g., PET fibers) can be introduced into the composite by depositing these fibers into the bands with absorbent material or including some absorbent material in the composite's distribution zones. The versatility of the method of the present invention enables the creation of unitary absorbent composites having a variety of compositions and absorbent properties.

The method of the present invention also allows for the deposition of foam dispersions (e.g., as bands of materials) into a fibrous slurry. In one embodiment, the composite includes wet-laid strata and foam-formed strata. In another embodiment, the composite includes a foam-formed strata. The ability to deposit a foam dispersion enables the use of a wide range of fiber types, lengths, and deniers in the composite's absorbent bands. By selection of fibers, the bands can be, for example, soft and have a degree of stretch. By forming a composite having stretch capabilities, a shaped core can be formed from a rectangular composite, thus eliminating the need to shape the by core by cutting, which results in material waste. Such a core also has the greatest density of absorbent material in the crotch area, the site of liquid insult.

As noted above, the absorbent composite of the present invention can be formed from furnishes including a combination of fibers and a binder in a dispersion medium, and absorbent material. In one embodiment, a fibrous slurry is formed by directly combining fibers and binder in a dispersion medium followed by the addition of absorbent material, preferably as a liquid suspension of chilled water, to an at least partially dewatered fibrous web on a foraminous support. In another embodiment, absorbent material is added to the partially dewatered fibrous web on a foraminous support in combination with fibers as a slurry containing fibers and absorbent material. Such a slurry can be prepared by first combining fibers with a dispersion medium to which is then added absorbent material in a second step.

Once the fibrous slurry is deposited onto the foraminous support, the dispersion medium begins to drain from the deposited slurry to provide an at least partially dewatered fibrous web. Removal of the dispersion medium (e.g., water) from the deposited fibrous slurry (i.e., the partially dewatered web) continues through, for example, the application of pressure, vacuum, and combinations thereof, and results in the formation of a wet composite.

The absorbent composite of the present invention is ultimately produced by drying the wet composite. Drying removes at least a portion of the remaining dispersion medium and water and provides an absorbent composite having the desired moisture content. Suitable composite drying methods include, for example, the use of drying cans, air floats and through air dryers. Other drying methods and apparatus known in the pulp and paper industry may also be used. Drying temperatures, pressures and times are typical for the equipment and methods used, and are known to those of ordinary skill in the art in the pulp and paper industry.

For foam methods, the fibrous slurry is an aqueous or foam slurry that further includes a surfactant. Suitable surfactants include ionic, nonionic, and amphoteric surfactants known in the art.

The deposition of the components of the absorbent composite onto the foraminous support ultimately results in the formation of a wet composite that includes absorbent material that may have absorbed water and, as a result, swollen in size. Water is withdrawn from the wet composite containing the water-swollen absorbent material distributed on the support and the wet composite dried.

In the methods of the present invention, the absorbent material preferably absorbs less than about 20 times its weight in the dispersion medium, more preferably less than about 10 times, and even more preferably less than about 1 time its weight in the dispersion medium. Other preferable absorbent materials include materials that absorb liquid only after prolonged contact with liquid, or that absorb liquid only under certain conditions, and do not absorb any significant amount of liquid during the forming process.

Foam methods are advantageous for forming the absorbent composite of the present invention for several reasons. Generally, foam methods provide fibrous webs that possess both relatively low density and relatively high tensile strength. For webs composed of substantially the same components, foam-formed webs generally have densities greater than air-laid webs and lower than wet-laid webs. Similarly, the tensile strength of foam-formed webs is substantially greater than for air-laid webs and approach the strength of wet-laid webs. Also, the use of foam-forming technology allows better control of the orientation and uniform distribution of fibers and the incorporation of a wide range of materials (e.g., long and synthetic fibers that cannot be readily incorporated into wet-laid processes) into the composite.

Figure 9:
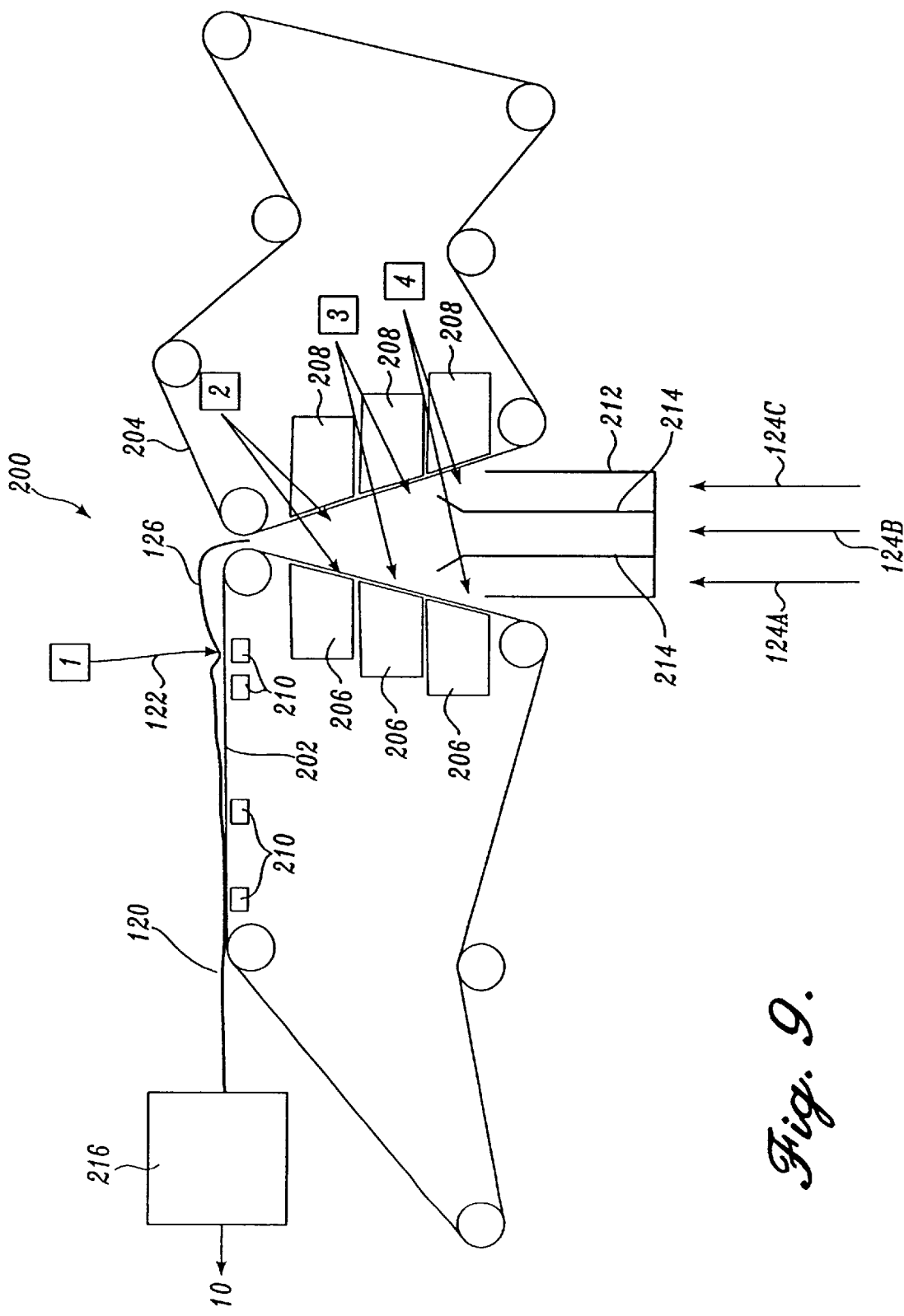
FIG. 9 is a diagrammatic view illustrating a twin-wire device and method for forming the composites of the invention.

The absorbent composite of the invention can be formed by devices and processes that include a twin-wire configuration (i.e., twin-forming wires). A representative twin-wire machine for forming composites of the invention is shown in FIG. 9. Referring to FIG. 9, machine 200 includes twin-forming wires 202 and 204 into which the composite's components are deposited. Basically, fibrous slurry 124 is introduced into headbox 212 and deposited onto forming wires 202 and 204 at the headbox exit. Vacuum elements 206 and 208 dewater the fibrous slurries deposited on wires 202 and 204, respectively, to provide partially dewatered webs that exit the twin-wire portion of the machine as partially dewatered web 126. Web 126 continues to travel along wire 202 and continues to be dewatered by additional vacuum elements 210 to provide wet composite 120 which is then dried by drying means 216 to provide composite 10.

Absorbent material can be introduced into the fibrous web at any one of several positions in the twin-wire process depending on the desired product configuration. For example, absorbent material can be introduced after the partially dewatered fibrous web has exited the twin-wire portion of the machine and has traveled along wire 202. Referring to FIG. 9, absorbent material 122 can be injected onto partially dewatered fibrous web 126 at position 1. Alternatively, absorbent material can be introduced into the partially dewatered fibrous web prior to the web exiting the twin-wire portion of the machine (i.e., in the headbox). Referring to FIG. 9, absorbent material 122 can be injected into the partially dewatered web at positions 2, 3, or 4, or other positions along wires 202 and 204 where the web has been at least partially dewatered. Absorbent material can be introduced into the partially dewatered web formed and traveling along wire 202 and/or 204. As noted above, to form the composite of the invention having bands of absorbent material extending in the composite's machine direction, absorbent material is injected into the partially dewatered fibrous webs by nozzles spaced laterally across the width of the web. The nozzles are connected to an absorbent material supply. The nozzles can be positioned in various positions (e.g., positions 1, 2, or 3 in FIG. 9) as described above. For example, referring to FIG. 9, nozzles can be located at positions 2 to inject absorbent material into partially dewatered webs on wires 202 and 204. Generally, the extent of mixing of fibers with absorbent material decreases as the fibrous web is dewatered (e.g., less mixing at position 1 than at position 2, and less mixing at position 2 than at position 3).

Depending on the position of absorbent material introduction, the twin-wire method for forming the composite of the present invention can provide a composite having a fibrous stratum. Representative composites of the invention having fibrous strata formed by the twin-wire method of the present invention are shown in FIGS. 10A–H. Referring to FIG. 10A, representative composites 10 include regions 112 enriched with absorbent material, distribution zones 114 substantially free of absorbent material, and fibrous strata 11 coextensive with the outward surfaces of composite 10.

Referring to FIG. 10A, composite 10 can be formed by a method that introduces absorbent material into a single partially dewatered web (i.e., a web traveling on wire 202 or 204). FIGS. 10B and 10C depict similarly formed composites having absorbent material extending into the composite to relatively greater depths (i.e., z-direction penetration). Referring to FIG. 10D, composite 10 includes absorbent material introduced into the center fibrous. Such a composite can be formed by adjusting the depth of absorbent material penetration by, for example, nozzle distance from the forming wire or absorbent material injection angle.

Alternatively, the composite of the invention can be formed by a twin-wire method that introduces absorbent material into both partially dewatered webs (i.e., webs traveling on wires 202 and 204). Such a method includes a two sets of nozzles, a first nozzle set for injection into one partially dewatered web, and a second nozzle set for injection into the other partially dewatered web. Referring to FIG. 10E, composite 10 includes regions enriched with absorbent material that extend substantially throughout the composite's depth (i.e., z-direction). Such a composite configuration can be formed from a pair of nozzle sets that are either positioned or timed to provide absorbent material bands that align in the z-direction. Offsetting one set of nozzles from the other, or providing nonsynchronous absorbent material pulses from a pair of aligned nozzle sets, provides composites having offset bands of absorbent material. Such a composite configuration is illustrated in FIG. 10F. FIGS. 10G and 10H illustrate composites formed by methods similar to those which provide the composites shown in FIGS. 10E and 10F, respectively, but in contrast to those composites, the composites of FIGS. 10G and 10H are formed by the introduction of absorbent material to a penetration depth less than that of the composites in FIGS. 10E and 10F.

As shown in FIG. 10, the composite of the present invention can include integrated phases having fibrous strata coextensive with the outward surfaces of the composite. These fibrous composites can be formed from multilayered inclined formers or twin-wire formers with sectioned headboxes. These methods can provide phased composites having strata or phases having specifically designed properties and containing components to attain composites having desired properties. The composite's regions of enriched absorbent material (i.e., the composite's absorbent bands) can be located throughout the z-direction by adjusting the basis weights of the upper and lower strata.

Basically, the position of the absorbent material band in the composite's z-direction effectively defines the fibrous stratum covering the band. For a formation method that includes a single fiber furnish, the band position can be adjusted by positioning the absorbent material injection system (e.g., nozzle set) in relation to the forming wire. For methods that include multiple furnishes, the upper and lower strata can be composed of the same or different components and introduced into a sectioned headbox.

Referring to FIGS. 9 and 10A, composite 10 having strata 11 can be formed by machine 200. For composites in which strata 11 comprise the same components, a single fiber furnish 124 is introduced into headbox 212. For forming composites having strata 11 comprising different components, headbox 212 includes one or more baffles (or dividers) 214 for the introduction of fiber furnishes (e.g., 124a, 124b, and 124c) having different compositions. In such a method, the upper and lower strata can be formed to include different components and have different basis weights and properties.

Preferably, the composite is formed by a foam-forming method using the components described above. In the foam-forming method, fibrous webs having multiple strata and including bands of absorbent material can be formed from multiple fibrous slurries. In a preferred embodiment, the foam-forming method is practiced on a twin-wire former.

The method can provide a variety of multiple strata composites including, for example, composites having three strata. A representative composite having three strata includes a first stratum formed from fibers (e.g., synthetic fibers, cellulosic, and/or binder fibers); an intermediate stratum formed from fibers and/or other absorbent material such as superabsorbent material; and a third stratum formed from fibers. The method of the invention is versatile in that such a composite can have relatively distinct and discrete strata or, alternatively, have gradual transition zones from stratum-to-stratum.

A representative method for forming a fibrous web having an intermediate stratum (i.e., a composite having three strata) generally includes the following steps:
(a) forming a first fibrous furnish comprising fibers in an aqueous dispersion medium;
(b) forming a second fibrous furnish comprising fibers in an aqueous dispersion medium;
(c) moving a first foraminous element (e.g., a forming wire) in a first path;
(d) moving a second foraminous element in a second path;
(e) passing the first furnish into contact with the first foraminous element moving in a first path;
(f) passing the second furnish into contact with the second foraminous element moving in the second path;
(g) passing a third material between the first and second furnishes such that the third material does not contact either of the first or second foraminous elements; and
(h) forming a fibrous web from the first and second furnishes and third material by withdrawing liquid from the furnishes through the first and second foraminous elements.

As noted above, the method is suitably carried out on a twin-wire former, preferably a vertical former, and more preferably, a vertical downflow twin-wire former. In the vertical former, the paths for the foraminous elements are substantially vertical. For foam-forming methods, the fibrous furnishes are foam furnishes and include a surfactant.

Figure 11:
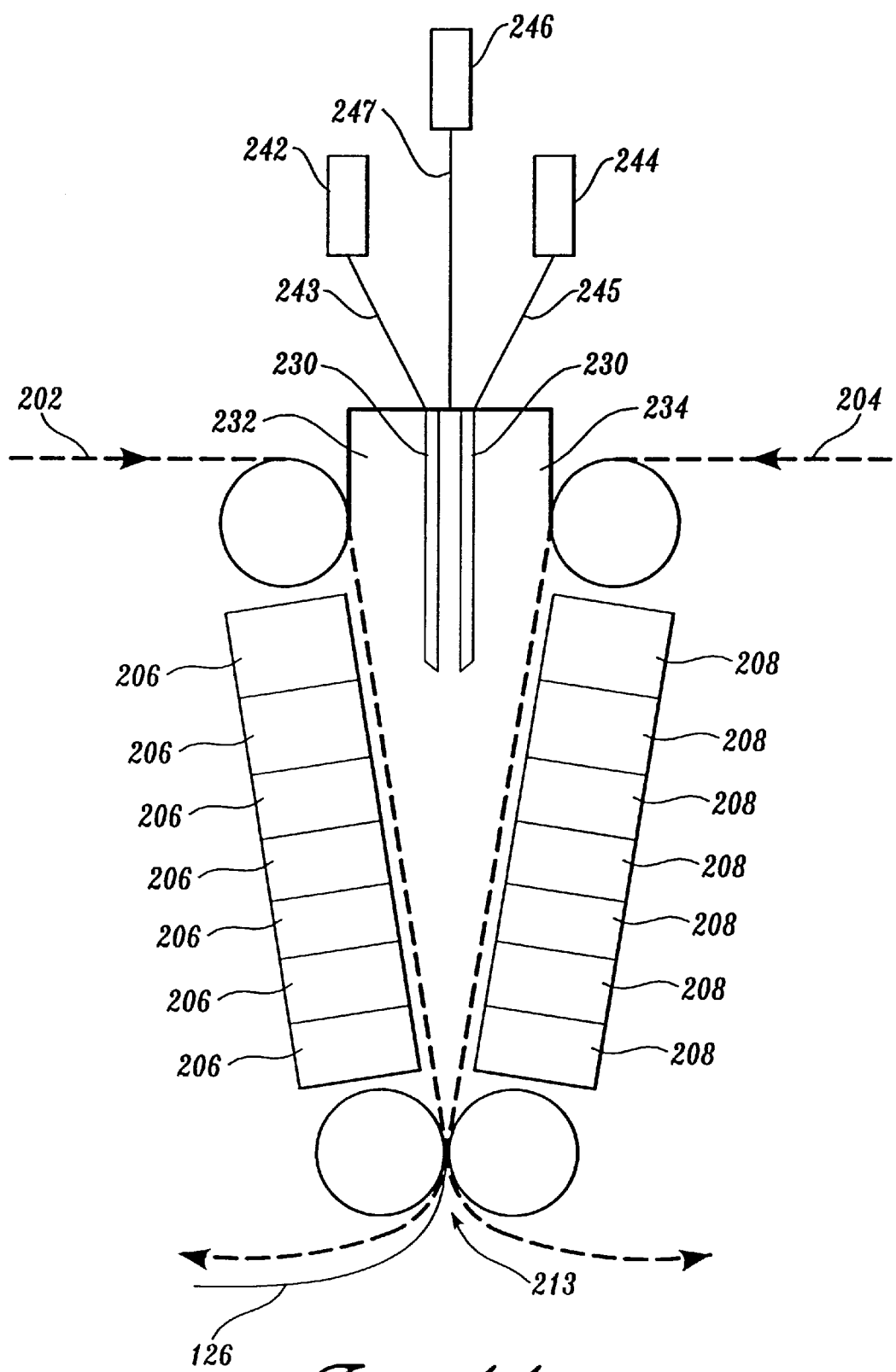
FIG. 11 is a diagrammatic view illustrating a headbox assembly and method for forming the composites of the invention.

A representative vertical downflow twin-wire former useful in practicing the method of the invention is illustrated in FIG. 11. Referring to FIG. 11, the former includes a vertical headbox assembly having a former with a closed first end (top), closed first and second sides and an interior volume. A second end (bottom) of the former is defined by moving first and second foraminous elements, 202 and 204, and forming nip 213. The interior volume defined by the former's closed first end, closed first and second sides, and first and second foraminous elements includes an interior structure 230 extending from the former first end and toward the second end. The interior structure defines a first volume 232 on one side thereof and a second volume 234 on the other side thereof. The former further includes supply 242 and means 243 for introducing a first furnish into the first volume, supply 244 and means 245 for introducing a second furnish into the second volume, and supply 246 and means 247 for introducing a third material into the interior structure. Means for withdrawing liquid (e.g., suction boxes 206 and 208) from the first and second slurries through the foraminous elements to form a web are also included in the headbox assembly.

In the method, the twin-wire former includes a means for introducing at least a third material through the interior structure in such a way that the third material forms bands or stripes in the resulting web. Preferably, the introducing means include at least a first plurality of conduits having a first effective length. A second plurality of conduits having a second effective length different from the first length may also be used. More than two sets of conduits can also be used.

Figure 12:
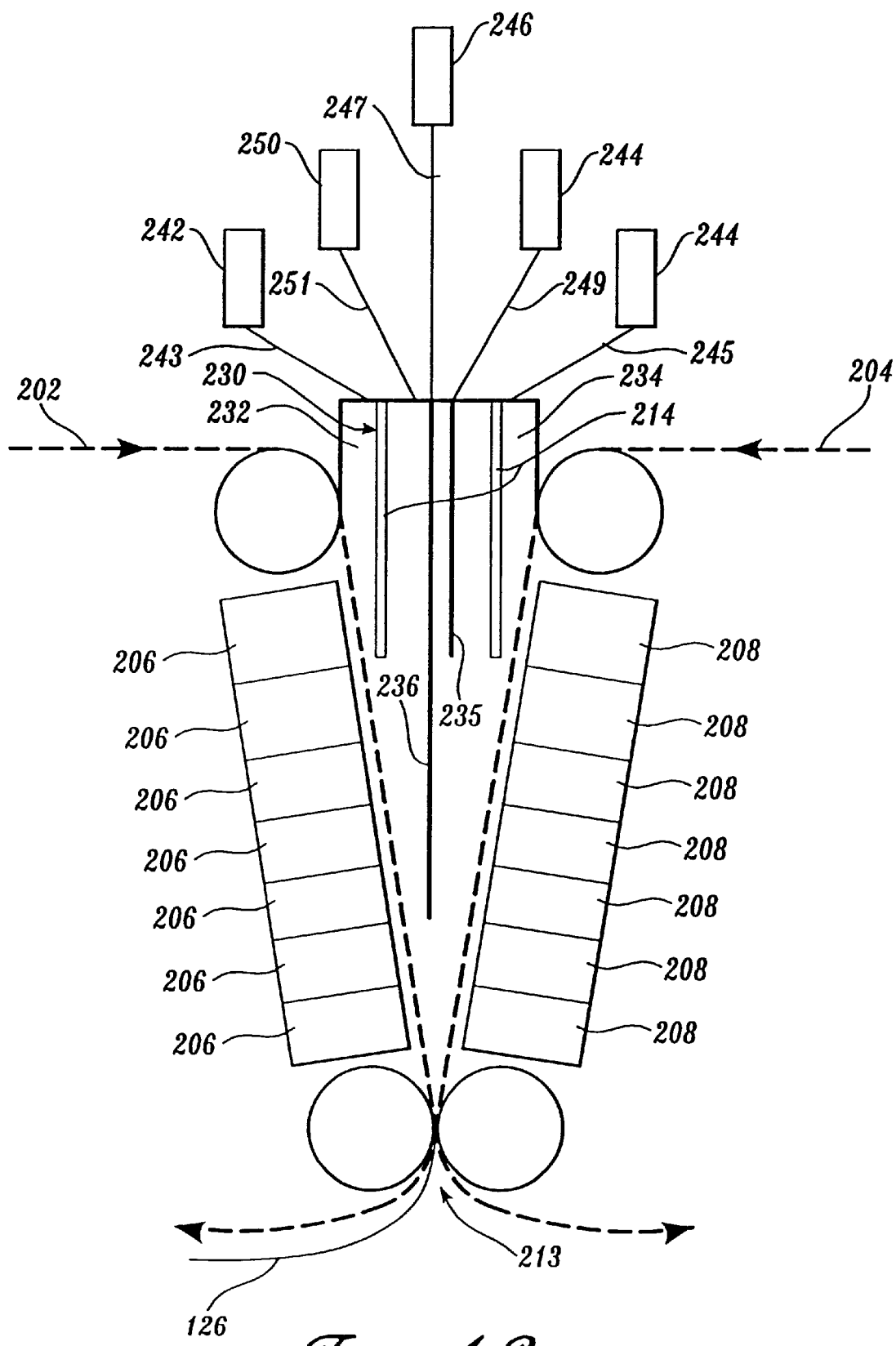
FIG. 12 is a diagrammatic view illustrating a headbox assembly and method for forming the composites of the invention.

Another representative vertical downflow twin-wire former useful in practicing the method of the invention is illustrated in FIG. 12. Referring to FIG. 12, the former includes a vertical headbox assembly having an interior volume defined by the former's closed first end, closed first and second sides, and first and second foraminous elements, 202 and 204, and includes an interior structure 230 extending from the former first end and toward the second end. In this embodiment, interior structure 230 includes plurality of conduits 235 and 236, and optional divider walls 214.

The interior structure defines a first volume 232 on one side thereof and a second volume 234 on the other side thereof The former further includes supply 242 and means 243 for introducing a first furnish into the first volume, supply 244 and means 245 for introducing a second furnish into the second volume, supply 246 and means 247 for introducing a third material into plurality of conduits 236, supply 248 and means 249 for introducing a third material into plurality of conduits 235, and supply 250 and means 251 for introducing another material, such as a foam slurry, within the volume defined by walls 214.

Figure 13:
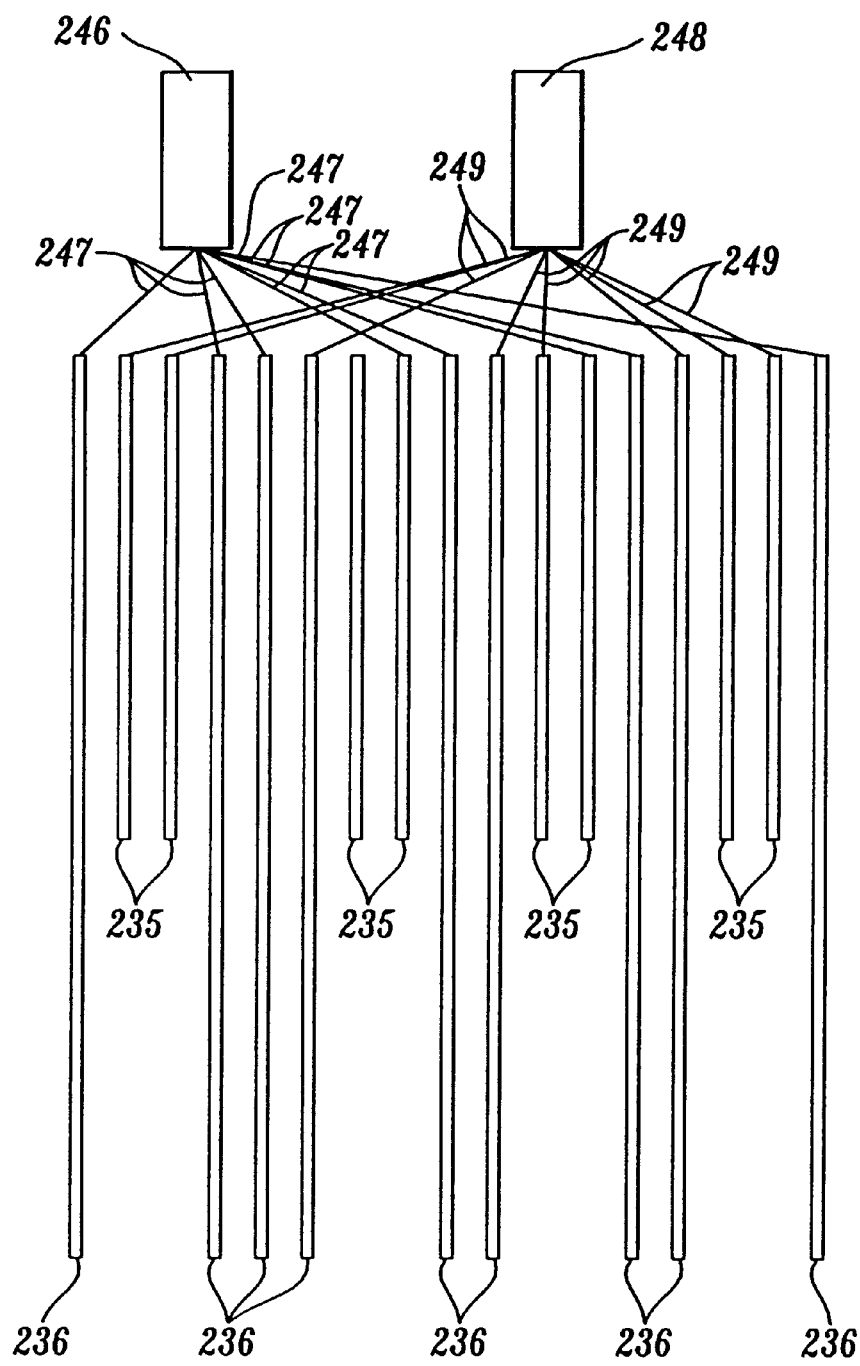
FIG. 13 is a diagrammatic view illustrating conduits for introducing materials into a fibrous web in accordance with the present invention.
Figure 14:
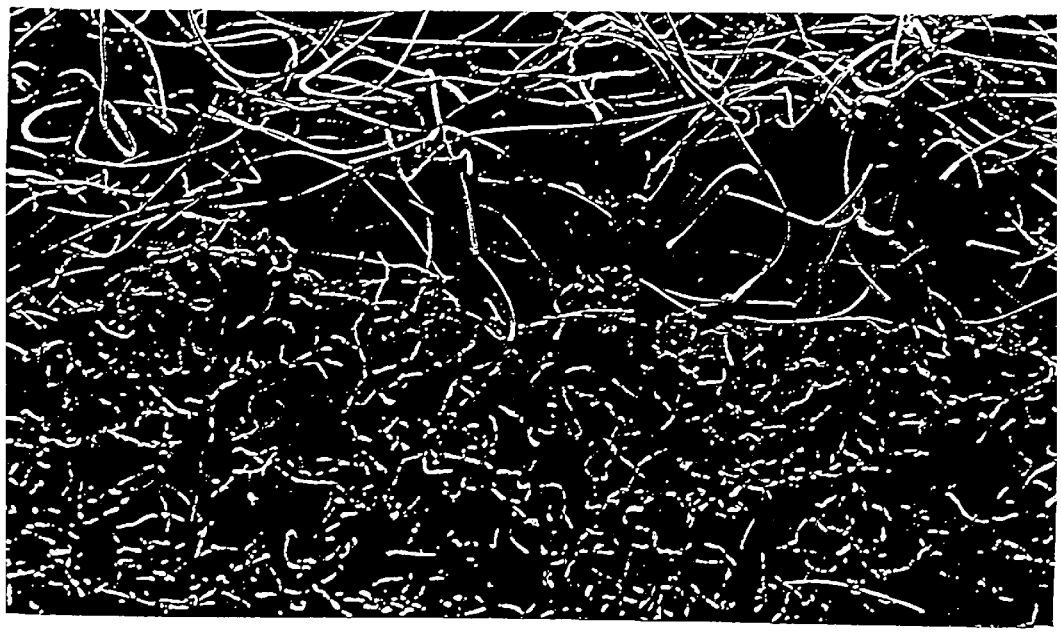
FIG. 14 is a photomicrograph (15.0× magnification) of a portion of a representative composite produced by an air-laid method in accordance with the present invention.
Figure 15:
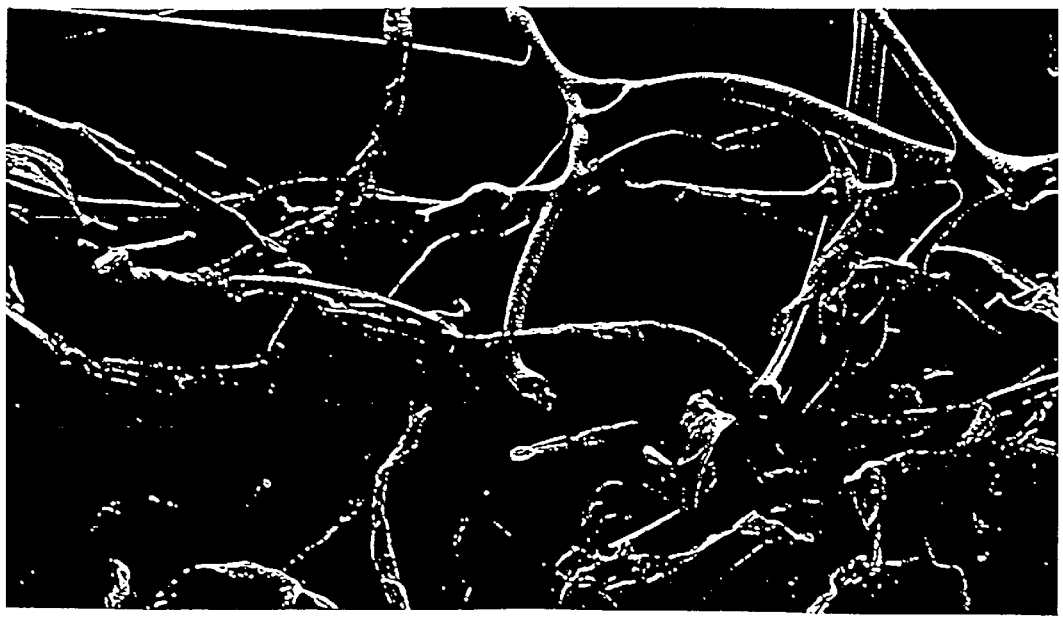
FIG. 15 is a photomicrograph (100× magnification) of a portion of the representative composite shown in FIG. 14.
Figure 16:
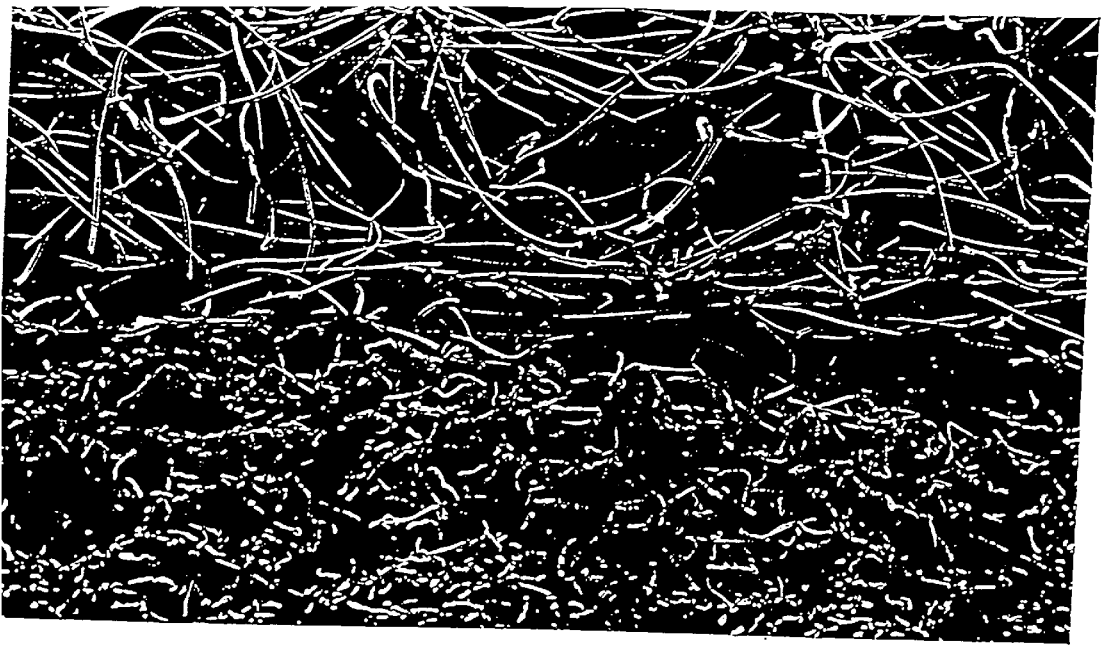
FIG. 16 is a photomicrograph (15× magnification) of a portion of a representative composite produced by a wet-laid method in accordance with the present invention.
Figure 17:
FIG. 17 is a photomicrograph (100× magnification) of a portion of the representative composite shown in FIG. 16.
Figure 18:
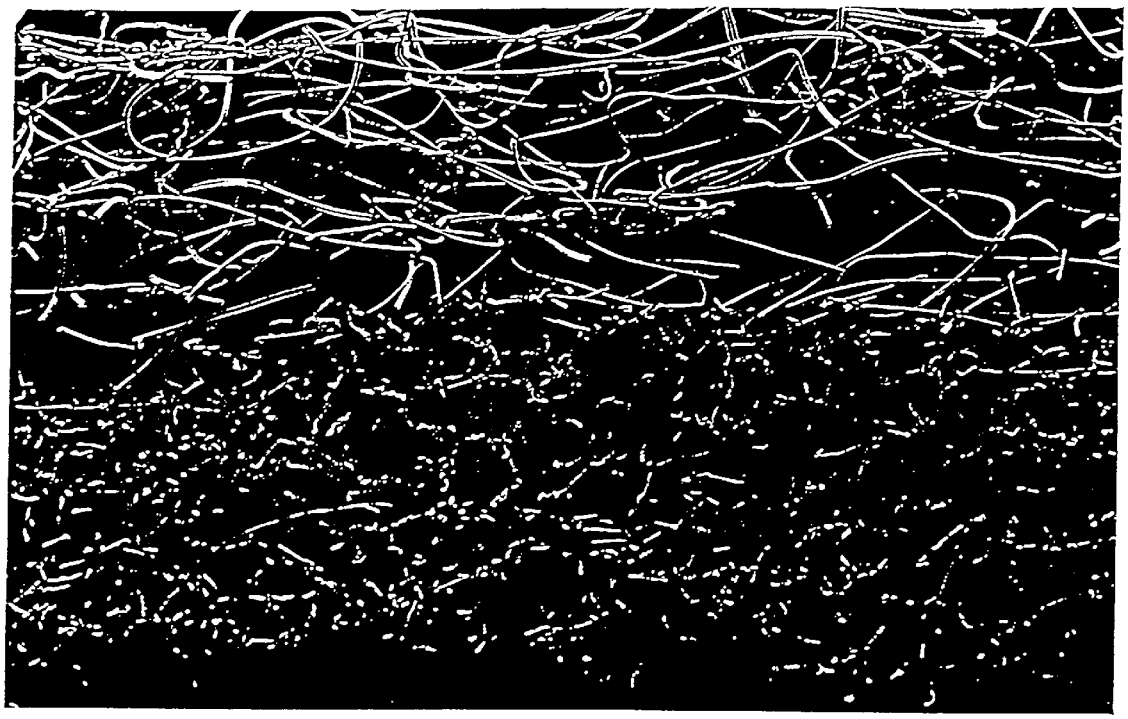
FIG. 18 is a photomicrograph (15× magnification) of a portion of a representative composite produced by a foam-formed method in accordance with the present invention.
Figure 19:
FIG. 19 is a photomicrograph (100× magnification) of a portion of the representative composite shown in FIG. 18.
Figure 20:
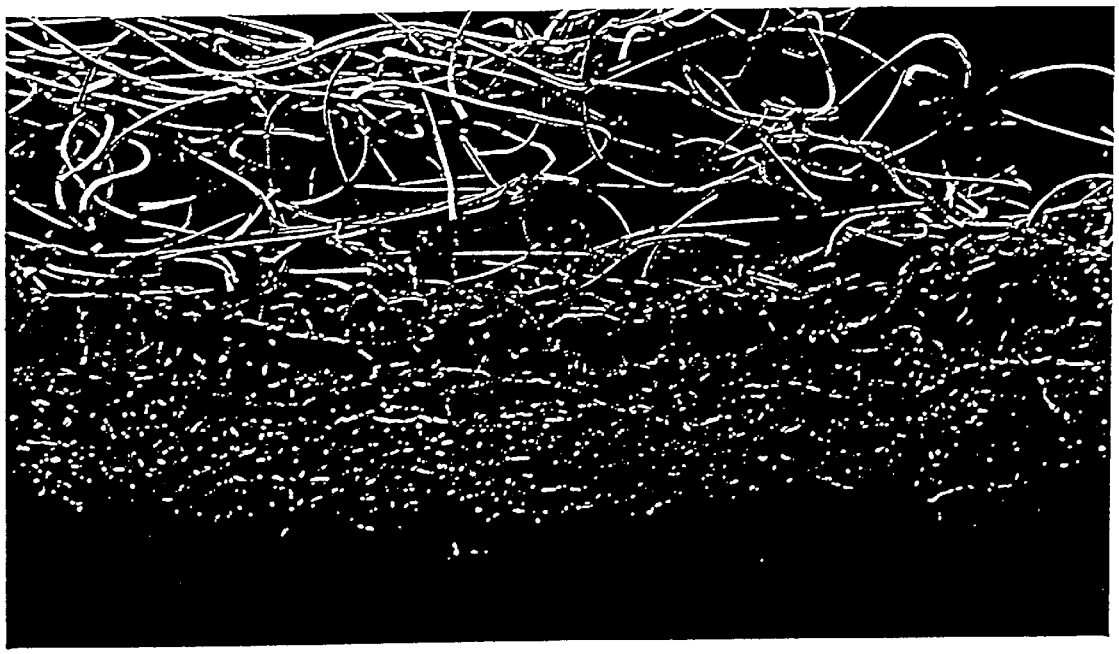
FIG. 20 is a photomicrograph (15× magnification) of a portion of a representative composite produced by a foam-formed method in accordance with the present invention.
Figure 21:
FIG. 21 is a photomicrograph (100× magnification) of a portion of the representative composite shown in FIG. 20.
Figure 12:
Figure 13:
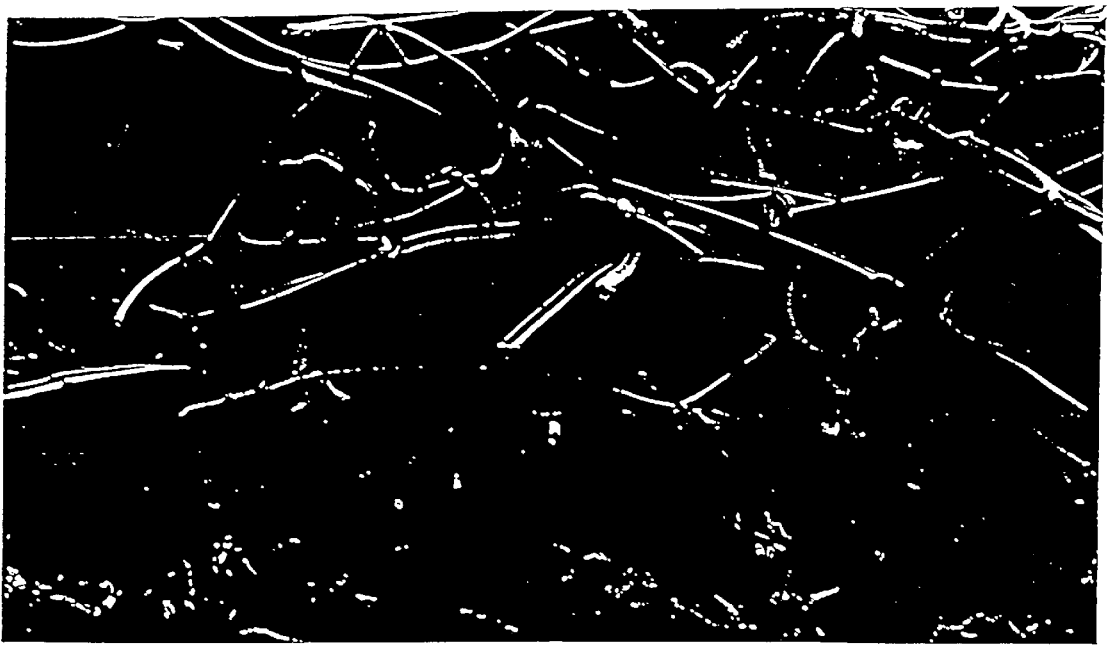

Plurality of conduits 235 can have an effective length different from plurality of conduits 236. The third material can be introduced through conduits 235 and 236, or, alternatively, a third material can be introduced through conduits 235 and a fourth material can be introduced through conduits 236. Preferably, the ends of conduits 235 and 236 terminate at a position beyond where the suction boxes begin withdrawing foam from the slurries in contact with the foraminous elements (i.e., beyond the point where web formation begins). Plurality of conduits 235 and/or 236 are suitable for introducing stripes or bands of third material in fibrous webs formed in accordance with the present invention. Plurality of conduits 235 and 236 can be moved in a first dimension toward and away from nip 213, and also in a second dimension substantially perpendicular to the first, closer to one forming wire or the other. Representative plurality of conduits 235 and 236 are illustrated in FIG. 13.

Generally, the former's interior structure (i.e., structure 230 in FIGS. 11 and 12) is positioned with respect to the foraminous elements such that material introduced through the interior structure will not directly contact the first and second foraminous elements. Accordingly, material is introduced through the interior structure between the first and second slurries after the slurries have contacted the foraminous elements and withdrawal of foam and liquid from those slurries has commenced. Such a configuration is particularly advantageous for introducing superabsorbent materials and for forming stratified structures in which the third material is a fiber furnish. Depending upon the nature of the composite to be formed, the first and second furnishes may be the same, or different, from each other and from the third material.

In a preferred embodiment, the method includes introducing the third material at a plurality of different points to provide a composite having bands or stripes of third material within the product. The positions of at least some of the plurality of different points for introducing the third material into the headbox can be adjusted when it is desired to adjust the introduction point in a first dimension toward and away from the headbox exit (i.e., nip 213 in FIGS. 12 and 13); and to adjust at least some of the plurality of points in a second dimension substantially perpendicular to the first dimension, closer to one forming wire or the other.

The method can also include utilizing a plurality of distinct conduits, the conduits being of at least two different lengths, for introducing the third material into the headbox. The method can also be utilized in headboxes having dividing walls that extend part of the length of the conduits toward the headbox exit. Such headboxes are illustrated in FIGS. 9 and 12.

The means for introducing first and second furnishes into the first and second volumes can include any conventional type of conduit, nozzle, orifice, header, or the like. Typically, these means include a plurality of conduits are provided disposed on the first end of the former and facing the second end.

The means for withdrawing liquid from the first and second furnishes through the foraminous elements to form a web on the foraminous elements are also included in the headbox assembly. The means for withdrawing liquid can include any conventional means for that purpose, such as suction rollers, pressing rollers, or other conventional structures. In a preferred embodiment, first and second suction box assemblies are provided and mounted on the opposite sides of the interior structure from the foraminous elements (see boxes 206 and 208 in FIGS. 9, 11, and 12).

The composites of the invention include at least two strata. The composition of each stratum (i.e., the components of the individual stratum) can be widely varied to provide widely varied composites having variable properties.

In a preferred embodiment, the present invention provides a unitary composite that is composed of a first stratum that includes a hydrophobic fibrous material that does not absorb bodily fluids and which forms an open and bulky stratum having a relatively low basis weight, and a second stratum that includes a hydrophilic fibrous material, such as crosslinked cellulose fibers, and having a basis weight preferably greater than the first stratum. Either one or both strata can also include a binder to effect bonding between the fibers of the first stratum, between the fibers of the second stratum, and between the fibers of the top and second strata of the unitary composite. The unitary composite can be incorporated into a variety of absorbent products and articles to provide rapid temporary storage capacity, to increase the liquid acquisition rate, to reduce leakage, and to improve the rewet and dry feel performance of the absorbent article.

Referring to FIG. 1, the unitary composite, indicated generally by reference numeral 10, includes a first stratum 12 and a second stratum 14. The first stratum of the unitary composite serves primarily as an acquisition stratum that can rapidly acquire liquid at the point of insult, and then rapidly and completely pass the liquid to the second stratum. The first stratum also serves as an antiwet back stratum having greater pore size and lower hydrophilicity than the second stratum. The second stratum serves to rapidly withdraw liquid from the first stratum and also serves as a temporary reservoir for the liquid gush associated with the release of bodily fluids. Representative composites formed in accordance with the present invention are shown in FIGS. 14–23. The substantially homogeneous individual fibrous strata are clearly apparent in FIGS. 14, 16, 18, and 20.

The composite's transition zone, which integrally connects the first and second strata and provides for intimate fluid communication, includes fibers from one stratum extending into the other. The transition zone can include hydrophobic fibers extending from the first stratum into the second stratum, as well as hydrophilic fibers extending from the second stratum into the first stratum. While the first stratum may be substantially coextensive with the second stratum, the transition zone is substantially coextensive with at least one of the composite's stratum. The unitary composite's transition zone is illustrated in FIGS. 14–23, which show representative composites formed in accordance with the present invention. Referring to these FIGURES, the transition zone is located in the composite generally between the substantially homogeneous regions of the individual strata and is defined as the region of the composite where the fibers from one stratum are commingled with fibers from the other stratum. The transition zone is clearly illustrated in FIGS. 22 and 23, which show the commingling of fibers extending from one stratum into the other for representative composites formed by air-laid, wet-laid, and foam-formed methods, respectively. Referring to FIGS. 22 and 23, the composite's transition zone is characterized by the commingling of relatively smooth, tubular hydrophobic fibers (i.e., polyethylene terephthalate fibers) of the first stratum with the relatively kinked, ribbon-shaped hydrophilic fibers (i.e., crosslinked cellulosic fibers) of the second stratum.

In one embodiment, the first stratum of the absorbent composite is generally a hydrophobic stratum that includes a hydrophobic fibrous material (i.e., one or more hydrophobic fibers). Other fibers, such as hydrophilic fibers, may be included in the first stratum as long as the overall first stratum remains relatively less hydrophilic than the second stratum. The first stratum can be composed of natural and/or synthetic fibers that do not significantly absorb bodily fluids, and that form an open (i.e., porous) and bulky stratum or web. The first stratum's pore size is preferably greater than the second stratum's and allows efficient fluid communication and drainage to the second stratum. Suitable synthetic fibers include, for example, polyethylene terephthalate (PET), polyethylene, polypropylene, nylon, latex, rayon. The synthetic fibers are present in an amount up to about 90% by weight of the first stratum. Suitable natural fibers include, for example, cotton, wool, wood pulp, straw, kenaf, and other cellulosic fibers. In a preferred embodiment, the second stratum includes crosslinked cellulosic fibers present in an amount up to about 90% by weight. The fibers noted above can optionally include one or more additives, such as wet strength agents, sizing agents, and surface active agents. The fibers noted above are commercially available from a number of suppliers including Hoechst Celanese, DuPont, Eastman Chemical, Hercules, Danaklon, Inc., and Weyerhaeuser Company. In a preferred embodiment, the first stratum includes a synthetic fiber and, more preferably, the first stratum includes polyethylene terephthalate.

Generally, the greatest rate of liquid acquisition is attained with composites having relatively low density. The formation of low-density composites can be achieved by varying the individual components of the composite. The performance of the unitary composite is dependent upon a number of factors including the fiber length, denier (g/m), crimping (crimps per inch), type of fiber treatment and physical and chemical nature of the fibers of the first stratum. Suitable fibers useful for construction of the first stratum have a length up to about 4 inches, and preferably have a length between about 0.25 and about 1.5 inches. Suitable fibers include fibers having denier up to about 40 denier, and preferably between about 5 and about 20 denier. While straight fibers can be advantageously used in the formation of the first stratum, in a preferred embodiment, the first stratum includes from about 50% to about 100% by weight of total crimped fibers. In a preferred embodiment, the fibers have up to about 30 crimps per inch and more preferably from about 1 to about 20 crimps per inch. In a most preferred embodiment, the first stratum includes 100% crimped fibers by weight of total fibers having from about 5 to about 15 crimps per inch. Thus, in a preferred embodiment, the first stratum includes polyethylene terephthalate fibers having relatively high denier, long length, and low crimp level.

In another preferred embodiment, the synthetic fibers include polyester fibers having morphologies other than the conventional homogeneous solid fibers noted above. Composites comprising hollow, deep-grooved, and lobal polyester fibers exhibit advantageous liquid acquisition characteristics. For example, deep-grooved fibers provide composites having low rewet, possibly due in part to improved capillary wicking in the grooves and more rapid liquid evaporation. Hollow fibers provide a composite having enhanced loft compared to composites that include homogeneous solid fibers. Lobal fibers (i.e., fibers having lobal cross-sectional shape) provide composites having a greater resistance to wet collapse compared to solid, round cross-sectioned fiber. For example, lobal polyester fibers are commercially available from Hoechst Celanese.

As noted above, the first stratum includes a binder. Suitable binders include, but are not limited to, cellulosic and synthetic fibrous materials, bonding agents, soluble bonding mediums, and wet strength agents. In one preferred embodiment, the binder includes bicomponent binding fibers, such as Celbond® (Hoechst Celanese) and D-271P® (DuPont). In another preferred embodiment, the binder includes a soluble binding medium, more preferably cellulose acetate used in combination with the solvent triacetin and/or triethyl citrate. For embodiments of the first stratum that include a binder, the binder is included in the stratum in an amount ranging from about 5% to about 50% by weight of the components of the first stratum. Preferably, the binder is integrally incorporated into or onto the fibrous web that is formed in the production of the unitary composite. The binder can be added to fibers prior to web formation, by applying the binder to the air-laid, wet-laid, or foam-formed web after web deposition, after drying, or a combination thereof.

Generally, the first stratum of the unitary composite has a basis weight of about 10 to about 100 g/m². The density of the first stratum can range from about 0.01 to about 0.3 g/cm³, and preferably from about 0.01 to about 0.08 g/cm³.

The second stratum of the unitary composite can be a hydrophilic stratum relative to the first stratum and include a hydrophilic fibrous material (i.e., one or more hydrophilic fibers). The second stratum can also include other fibers, such as hydrophobic fibers (e.g., synthetic fibers such as polyester fibers including polyethylene terephthalate fibers), and these fibers can be included in the second stratum in an amount up to about 90% by weight of the stratum, provided that the overall stratum remains relatively, hydrophllic compared to the first stratum. The second stratum can also include mixtures of hydrophilic and synthetic fibers. Further, the second stratum has smaller pores than the first stratum, thereby facilitating fluid communication between the strata and drainage from the first stratum. In a preferred embodiment, the hydrophilic fibers include cellulosic fibers in an amount up to about 90% by weight of the stratum, and more preferably crosslinked cellulosic fibers in an amount up to about 90% by weight of the stratum. In another preferred embodiment, the cellulosic fibers include chemithermomechanical pulp fibers. Suitable and preferred cellulosic fibers are described above.

Alternatively, in another embodiment, the second stratum does not include cellulosic fibers. In this embodiment, the stratum comprises synthetic fibers in an amount up to about 95% by weight and binder in an amount from about 5 to about 50% by weight.

To further improve storage capacity and/or liquid acquisition and wicking of the absorbent composite, in another embodiment either the first or second strata include a superabsorbent polymeric material.

In addition to hydrophilic fibers, the second stratum also includes a binder. Suitable binders for the fibers of the second stratum include, but are not limited to, those noted above and described in more detail above. The binder is preferably present in an amount ranging from about 5% to about 50% by weight of the components of the second stratum.

The second stratum generally has a basis weight of from about 10 to about 500 g/m$^2$. The second stratum has a density from about 0.03 to about 0.5 g/cm$^3$, and preferably from about 0.03 to about 0.1 g/cm$^3$.

The second stratum is generally characterized as having a smaller pore size and increased hydrophilicity relative to the first stratum. Thus, the acquired liquid flows away from the first stratum to the more hydrophilic second stratum having smaller pores. Furthermore, because the pore size of the second stratum is less than the pore size of the first stratum, a pore size gradient is created that provides liquid drainage away from the first stratum. The intimate commingling between the fibers of the first and second stratum of the unitary composite provided by the transition zone enables more efficient drainage of the first stratum and fluid communication between the two strata than in other absorbent products formed from separate and distinct acquisition and storage layers.

The second stratum primarily serves to rapidly draw liquid from the first stratum. The second stratum also acts to temporarily store liquid acquired by the absorbent composite and prevent flow back to and beyond the first stratum. Depending upon the nature of the absorbent construct, an absorbent article incorporating the unitary composite may include one or more additional strata, such as a permanent storage. In such a construct, in addition to rapidly absorbing the acquired liquid from the first stratum, the second stratum has absorbent capacity sufficient to temporarily hold the acquired liquid and therefore provide time sufficient for the core stratum to permanently absorb the liquid from the absorbent composite.

In one embodiment of the composite described above, the overall absorbent composite includes a hydrophilic fibrous material (i.e., one or more hydrophllic fibers) present in the absorbent composite in an amount from about 40% to about 90% by weight of the total composite, a hydrophobic fibrous material (i.e., one or more hydrophobic fibers) present in the composite in an amount from about 1% to about 60% by weight of the total composite, and a binder present in the composite in an amount from about 5% to about 30% by weight of the total composite. Preferably, the hydrophilic fibers are present in the composite in about 60% to about 80% by weight of the total composite, the hydrophobic fibers are present in the composite in about 5% to about 20% by weight of the total composite, and a binder present in the composite in the amount of about 10% to about 20% by weight of the total composite. The unitary composite generally has a basis weight of from about 20 to about 600 g/m$^2$, and preferably from about 50 to about 360 g/m$^2$.

Generally, the absorbent composite has a density from about 0.01 to about 0.4 g/cm$^3$, and preferably from about 0.03 to about 0.15 g/cm$^3$. In one embodiment, the unitary composite is a densified composite. Densification methods useful in producing the densified composites are well known to those in the art. Densified unitary composites generally have a density from about 0.1 to about 0.5 g/cm$^3$, and preferably from about 0.1 to about 0.25 g/m$^3$.

For certain applications, the unitary composite is an undensified composite. Accordingly, production methods used in connection with the absorbent composite preferably do not include subjecting the absorbent composite, or absorbent articles that incorporate the absorbent composite, to densification conditions. For example, in the production of diapers that incorporate the absorbent composite of the present invention, the absorbent composite is preferably incorporated into the diaper after the diaper has been subjected to the application of pressure such as, for example, being passed through a calender roll.

Unitary composites of the present invention can include multiple strata formed from multiple furnishes that can have widely differing compositions. Unitary composites having two strata are described in international patent application Serial No. PCT/US97/22342, UNITARY STRATIFIED COMPOSITE, assigned to Weyerhaeuser Company, the assignee of the present application, and incorporated herein by reference in its entirety. The unitary composite of this invention can include a stratum as described in international patent application Serial No. PCT/US97/22341, UNITARY ABSORBENT LAYER, assigned to Weyerhaeuser Company, the assignee of the present application, and incorporated herein by reference in its entirety. Such a stratum can be useful as an acquisition and/or distribution layer in a composite in combination with other strata.

For other applications, the unitary composite is a densified composite. In these composites, one or more of the strata incorporate fibers that are readily densified and thus preferentially compacted in the densified composite. Readily densified fibers include resilient and anfractuous fibers including crosslinked fibers and other fibers such as CTMP fibers. For these composites, the entire composite is compressed by, for example, calendering. The result is a composite having a densified stratum or strata. On contact with liquid, the composite absorbs liquid and the densified stratum absorbs liquid and expands. The expansion of the stratum on liquid contact recreates void space lost on densification and results in a temporary storage capacity increase for the stratum and the composite. In a preferred embodiment, the density of the densified stratum is in the range from about 0.1 to about 0.6 g/m$^2$.

Composites that include densified strata generally include the stratum as an acquisition and/or distribution stratum. Liquid acquired by the expanded stratum can ultimately be delivered to a storage stratum.

In another embodiment, the unitary composite can include a liquid impervious surface. In this embodiment, a liquid impervious or liquid impermeable surface is created on a surface of the composite. To achieve this liquid barrier, the outward surface of a composite (i.e., an outward stratum) is treated either chemically or mechanically to provide the liquid impervious surface. Chemical treatments include the application of a material capable of forming a liquid impervious film. Mechanical treatments include the application of pressure and/or heat to a stratum that responds to such a treatment resulting in the formation of the impervious surface. Suitable strata include fibrous materials capable of effectively receiving such treatment are compressible and/or bondable and can include synthetic fibers or cellulosic fibers such as eucalyptus fibers, microfibers (e.g., microfibriliated fibers), and their mixtures.

In one embodiment, the liquid impervious surface is a densified surface having a density in the range from about 0.3 to about 0.7 g/cm$^3$.

The treatment can be performed over the entire surface of the stratum to provide a liquid impervious surface. Alternatively, the treatment can be performed over a portion of the stratum surface creating regions of liquid imperviousness or liquid barriers. The formed fibrous web can be treated with, for example, a rotating compression drum that applies a chemical and/or pressure and/or heat to a web that is receptive to such treatment. In such a method for application, the rotating drum can be embossed so as to create treatment patterns on the composite surface. Representative patterns include patterns that run in the machine direction of the web and patterns that run in the cross-machine direction. Typically, these barriers serve to stop liquid flow and thereby contain liquid in the composite. In addition to providing composites with entire surface treatments, such treatments can also provide composites having edges that prevent liquid flow from escaping the composite.

Unitary composites of the present invention can include multiple strata formed from multiple furnishes that can have widely differing compositions. For example, the absorbent composite of the present invention can include one or more strata that include absorbent material. In such embodiments, the absorbent material can be distributed substantially throughout the stratum and serves to absorb and retain liquid acquired by the composite. In a preferred embodiment, the absorbent material is a superabsorbent material. In addition to forming a matrix for the absorbent material, the stratum's fibers provide a stable three-dimensional network of channels or capillaries that serve to acquire liquid contacting the composite and to distribute the acquired liquid to the absorbent material. Generally, the absorbent material-containing stratum includes a wet strength agent that further increases tensile strength and structural integrity of the stratum and composite.

In one embodiment, the stratum is a fibrous matrix that includes absorbent material. The fibrous matrix defines voids and passages between the voids, which are distributed throughout the stratum. Absorbent material is located within some of the voids. The absorbent material located in these voids is expandable into the void.

Because the stratum is highly absorbent having a high liquid storage capacity, the stratum can be incorporated into a composite and included in an absorbent article as a liquid storage core. In such a construct, the composite can be combined with one or more other composites, layers, or strata, including, for example, an acquisition and/or distribution layer or strata. Because of the stratum's capacity to rapidly acquire and distribute liquid, the stratum can serve as a liquid management layer that acquires and transfers a portion of the acquired liquid to an underlying storage layer. Thus, in another embodiment, the stratum can be combined with a storage layer to provide an absorbent core that is useful in absorbent articles.

Preferably, the absorbent material-containing stratum is a reticulated absorbent composite. As used herein, the term "reticulated" refers to the stratum's open and porous nature characterized as having a stable three-dimensional network of fibers (i.e., fibrous matrix) that create channels or capillaries that serve to rapidly acquire and distribute liquid throughout the stratum, ultimately delivering acquired liquid to the absorbent material that is distributed throughout the stratum.

The reticulated stratum is an open and stable structure. The fibrous stratum's open and stable structure includes a network of capillaries or channels that are effective in acquiring and distributing liquid throughout the stratum. In the stratum, fibers form relatively dense bundles that direct fluid throughout the stratum and to absorbent material distributed throughout the stratum. The stratum's wet strength agent serves to stabilize the fibrous structure by providing interfiber bonding. The interfiber bonding assists in providing a stratum having a stable structure in which the stratum's capillaries or channels remain open before, during, and after liquid insult. The stratum's stable structure provides capillaries that remain open after initial liquid insult and that are available for acquiring and distributing liquid on subsequent insults.

Figure 24:
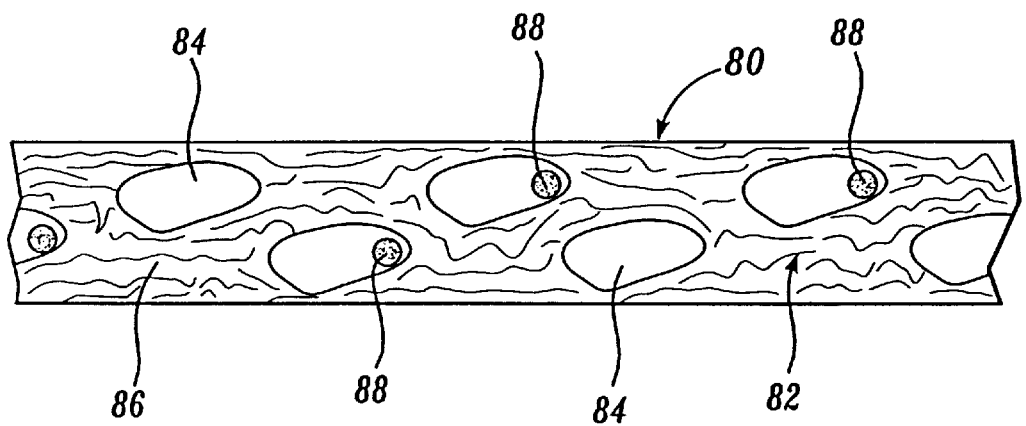
FIG. 24 is a cross-sectional view of a representative absorbent-material containing stratum of a composite formed in accordance with the present invention.

Referring to FIG. 24, a representative reticulated stratum, indicated generally by reference numeral 80, formed in accordance with the present invention is a fibrous matrix that includes fibrous regions 82 substantially composed of fibers 86 and defining voids 84. Some voids include absorbent material 88. Voids 84 are distributed throughout composite 80.

Representative reticulated strata include 48 percent by weight matrix fibers (i.e., southern pine commercially available from Weyerhaeuser Co. under the designation NB416), 12 percent by weight resilient fibers (i.e., crosslinked fibers), 40 percent by weight absorbent material (i.e., superabsorbent material commercially available from Stockhausen), and about 0.5 percent by weight wet strength agent (i.e., polyamide-epichlorohydrin resin commercially available from Hercules under the designation Kymene®). In these strata, fibrous regions extend throughout the composite, creating a network of channels. Void regions, including those that include absorbent material, appear throughout the composite and are in fluid communication with the composite's fibrous regions. Absorbent material appears in the composite's voids, generally surrounded by dense fiber bundles. On liquid contact, absorbent material in the strata swell and increased in size to more fully occupy voids that the absorbent material previously occupied in the dry composite.

As noted above, the stratum's voids are formed by the hydration and swelling of absorbent material (i.e., during wet composite formation) and the subsequent dehydration and decrease in size of the absorbent material (i.e., during wet composite drying). Ultimately, the density of the stratum and composite depends on the extent to which the absorbent material absorbs liquid and swells during the formation of the wet composite, and the conditions and extent to which the wet composite incorporating the swollen absorbent material is dried. Water absorbed by the absorbent material during wet composite formation is removed from the absorbent material, decreasing its size, on drying the wet composite. The dehydration of the swollen absorbent material defines some of the voids in the fibrous stratum.

The unitary composite of this invention can include an absorbent material-containing stratum as described above and as described in international patent application Serial No. PCT/US98/09682, RETICULATED ABSORBENT COMPOSITE, and U.S. patent application Ser. No. 60/107, 998, both assigned to Weyerhaeuser Company, the assignee of the present application, and incorporated herein by reference in their entireties. The composite of the invention can also include an absorbent material-containing stratum in which the absorbent material is located in discrete positions and/or configurations (e.g., bands or flutes) as described in international patent applications Serial No. PCT/US99/05998, FLUTED COMPOSITE AND RELATED ABSORBENT ARTICLES, and Serial No. PCT/US99/05997, METHODS FOR FORMING A FLUTED COMPOSITE, both assigned to Weyerhaeuser Company, the assignee of the present application, and incorporated herein by reference in their entireties. As noted above, such absorbent material-containing strata can be useful as a storage strata in a composite in combination with other strata.

Absorbent composites formed in accordance with the present invention can be advantageously incorporated into a variety of absorbent articles such as diapers including disposable diapers and training pants; feminine care products including sanitary napkins, and pant liners; adult incontinence products; toweling; surgical and dental sponges; bandages; food tray pads; and the like. Because the composite can be highly absorbent, the composite can be included into an absorbent article as a liquid storage core. In such a construct, the composite can be combined with one or more other composites or layers including, for example, an acquisition and/or a distribution layer. Alternatively, because the composite can rapidly acquire, distribute, and store liquid, the composite can be effectively incorporated into an absorbent article as the sole absorbent component without including other individual layers such as acquisition and/or distribution layers. In a preferred embodiment, the present invention provides an absorbent article, such as a diaper, that includes an absorbent composite having a liquid pervious facing sheet and a liquid impervious backing sheet. Furthermore, because the composite can have the capacity to rapidly acquire and distribute liquid, the composite can serve as a liquid management layer that acquires and transfers a portion of the acquired liquid to an underlying storage core. Thus, in another embodiment, the absorbent composite can be combined with a storage core to provide an absorbent core that is useful in absorbent articles.

Figure 25:
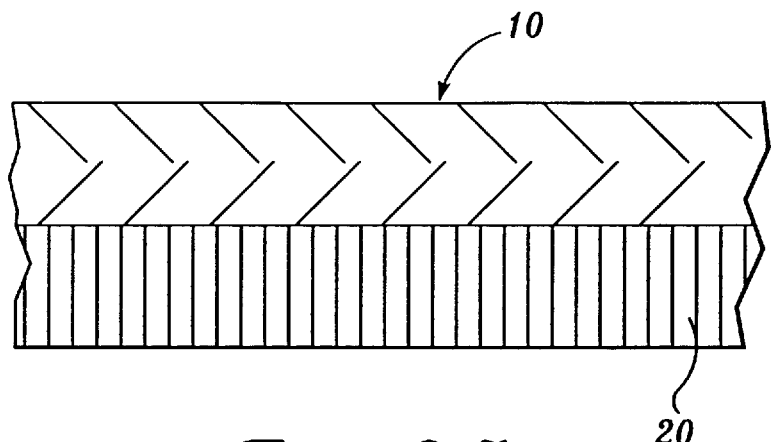
FIG. 25 is a cross-sectional view of a representative absorbent construct incorporating a composite formed in accordance with the present invention.
Figure 26:
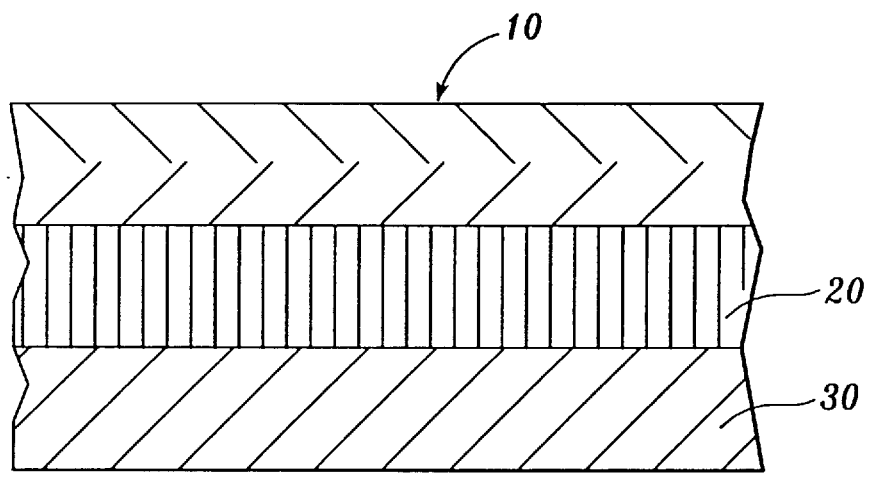
FIG. 26 is a cross-sectional view of another representative absorbent construct incorporating a composite formed in accordance with the present invention.
Figure 27:
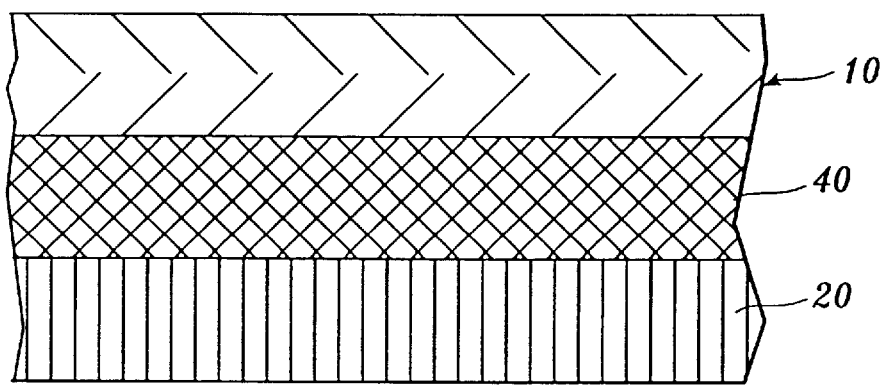
FIG. 27 is a cross-sectional view of a further representative absorbent construct incorporating a composite formed in accordance with the present invention.

As noted above, the unitary composite 10 of the present invention includes a first stratum 12 and a second stratum 14 as schematically depicted in FIG. 1. In the following FIGURES the unitary composite of the invention is illustrated schematically. It will be appreciated that schematically illustrated unitary composite 10 refers to all of the unitary composites of the invention including the representative composites shown in FIGS. 1 and 3–6. The composite can be incorporated in an absorbent article as the absorbent stratum. The absorbent composite can be used alone or, as illustrated in FIG. 25, can be used in combination with one or more secondary strata. In FIG. 25, the absorbent composite is employed as an upper acquisition/distribution stratum in combination with a storage stratum 20 composed of, for example, a fibrous web. Storage stratum 20, if desired, can also comprise a densified stratum of bonded cellulose fibers. As illustrated in FIG. 26, a third stratum 30 (e.g., a core or retention stratum) can also be employed, if desired, with a storage stratum 20 and absorbent 10. If desired, the retention stratum 30 can also be composed of a fibrous web such as, for example, densified bonded cellulose fibers. Alternatively, a distribution stratum 40 can be interposed between absorbent 10 and storage stratum 20 as illustrated in FIG. 27. Distribution stratum 40 is generally a hydrophilic fibrous material that includes, for example, hydrophilic fibers such as cellulosic fibers, preferably crosslinked cellulosic fibers, and a binder. In one preferred embodiment, the cellulosic fibers are crosslinked eucalyptus fibers. Distribution stratum 40 can optionally include superabsorbent polymeric material.

Figure 28:
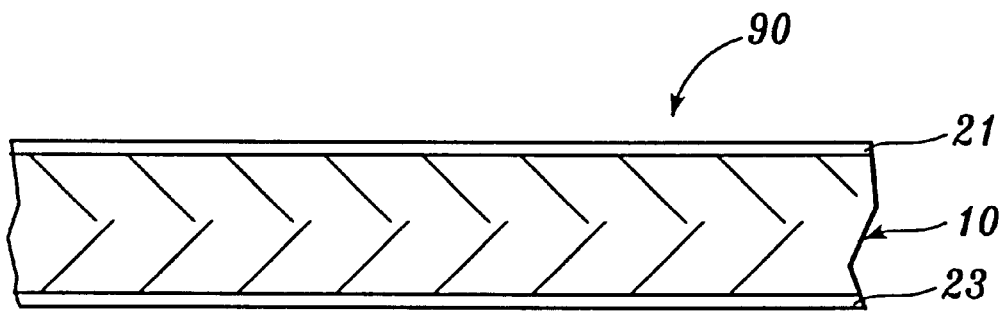
FIG. 28 is a cross-sectional view of a representative absorbent article incorporating a composite formed in accordance with the present invention.
Figure 29:
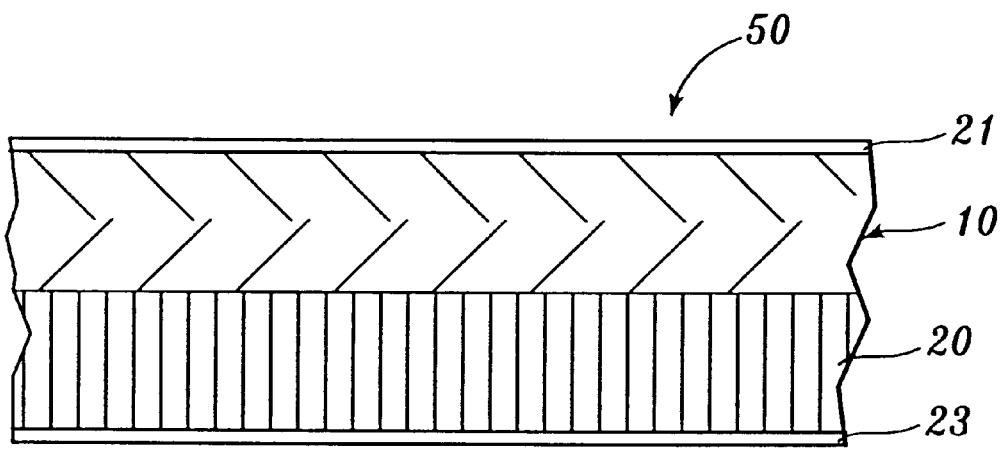
FIG. 29 is a cross-sectional view of a another representative absorbent article incorporating a composite formed in accordance with the present invention.

A variety of suitable absorbent articles can be produced from the unitary composite. The most common include absorptive consumer products such as diapers, feminine hygiene products such as feminine napkins, and adult incontinence products. The composite of the invention can be used alone, or in combination with other layers or composites, to provide an absorbent structure for incorporating into an absorbent article. For example, referring to FIG. 28, absorbent article 90 includes representative composite 10, topsheet 21, and backsheet 23. In all of the absorbent articles described herein, the composite is generally secured within the topsheet and backsheet, which can be secured to each other. Referring to FIG. 29, an absorbent article 50 includes absorbent composite 10 and an underlying storage stratum 20. A liquid pervious facing sheet 21 overlies absorbent composite 10 and a liquid impervious backing sheet 23 underlies the storage stratum 20. The unitary composite will provide advantageous liquid acquisition performance for use in, for example, diapers. The capillary structure of the absorbent composite will aid in fluid transport in multiple wettings. Generally, the storage stratum 20 includes a fibrous web, for example, a strengthened web of cellulose fibers, and may also incorporate additives, such as superabsorbent polymers to significantly increase the absorbent capacity of the storage stratum 20.

The article of FIG. 29 can be assembled so that absorbent composite 10 is brought into contact with the storage stratum 20 while the binder in the latter is still active. Such a procedure will allow the storage stratum to bond to at least the lower surface of absorbent 10, and thus eliminate the need to use hot-melt glues to bond adjacent strata.

A stronger bond between absorbent composite 10 and the storage stratum 20 can be achieved by contacting the absorbent composite with the storage stratum while the absorbent composite's binder is still active. Similarly, laying the storage stratum 20 on the backing sheet 23 while the binder of the storage stratum is still active results in the bonding of stratum 20 to the backing sheet 18. In a similar manner, absorbent composite 10 may be bonded to the facing sheet 21 by laying the facing sheet on absorbent composite 10 while the binder therein is still active. Interbonding between strata can enhance and further facilitate fluid transport across the stratum interface.

Figure 30:
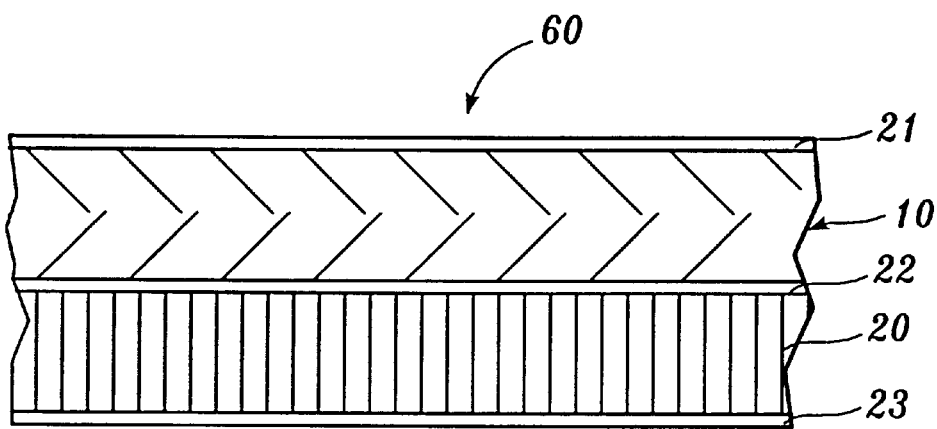
FIG. 30 is a cross-sectional view of a further representative absorbent article incorporating a composite formed in accordance with the present invention.

The construct in FIG. 29 is shown for purposes of exemplifying a typical absorbent article, such as a diaper or feminine napkin. One of ordinary skill will be able to make a variety of different absorbent constructs using the concepts taught herein. For example, a typical construction for an adult incontinence absorbent structure is shown in FIG. 30. The article 60 comprises a facing sheet 21, absorbent composite 10, a storage stratum 20, and a backing sheet 23. The facing sheet 21 is pervious to liquid while the backing sheet 23 is impervious to liquid. In this construct, a liquid pervious tissue 22 composed of a polar, fibrous material is positioned between absorbent composite 10 and storage stratum 20.

Figure 31:
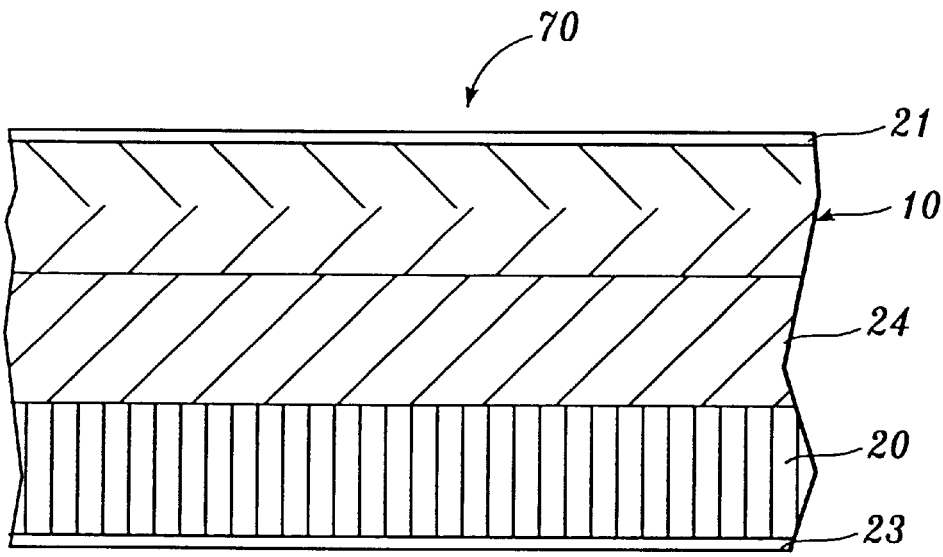
FIG. 31 is a cross-sectional view of a still another representative absorbent article incorporating a composite formed in accordance with the present invention.

Referring to FIG. 31, another absorbent article 70 includes a backing sheet 23, a storage stratum 20, an intermediate stratum 24, an absorbent composite 10, and a facing sheet 21. The intermediate stratum 24 contains, for example, a densified fibrous material such as a combination of cellulose acetate and triacetin, which are combined just prior to forming the article. The intermediate stratum 24 can thus bond to both the absorbent composite 10 and the storage stratum 20 to form an absorbent article with much more integrity than one in which the absorbent composite and storage stratum are not bonded to each other. The hydrophilicity of stratum 24 can be adjusted in such a way as to create a hydrophilicity gradient among strata 10, 24, and 20. It should be understood that an independent intermediate stratum is not required in order to get stratum-to-stratum bonding. When one of two adjacent strata or both strata contain a binder, if the two strata are brought together when the bonding medium is still active, bonding between the two strata will occur and provide a stronger composite compared to a composite lacking any bonding. Alternatively, intermediate stratum 24 can be a distribution stratum as described above in reference to the construct of FIG. 27.

The unitary composite of the present invention improves the surface dryness rewet performance, and acquisition rate of absorbent products and articles that incorporate the absorbent composite. The absorbent composite also provides increased pad integrity, improved appearance, and a reduction in wet collapse during use for absorbent products that incorporate the absorbent composite. Furthermore, because the unitary composite can be manufactured and delivered in web form, absorbent product manufacturing processes that include the absorbent composite are simplified relative to manufacturing processes that involve the handling of bales of crosslinked fibers or fluff pulp. Thus, in addition to the increased performance provided to absorbent products that incorporate the absorbent composite of this invention, the absorbent composite offers economic advantages over the combination of separate strata of high-loft nonwoven fibers and crosslinked cellulose.

While the preferred embodiment of the invention has been illustrated and described, it will be appreciated that various changes can be made therein without departing from the spirit and scope of the invention.

What is claimed is:

1. An absorbent composite comprising a first stratum, a second stratum, a third stratum, a first transition zone intermediate and coextensive with the first and second strata, and a second transition zone intermediate and coextensive with the second and third strata;
   the first stratum comprising first fibers and a binder;
   the second stratum comprising second fibers and a binder;
   the third stratum comprising third fibers and a binder;
   the first transition zone comprising fibers from the first and second strata commingled substantially uniformly across the composite's width and along the composite's length; and
   the second transition zone comprising fibers from the second and third strata commingled substantially uniformly across the composite's width and along the composite's length.

2. The composite of claim 1 wherein the first, second, and third strata comprise fibers selected from the group consisting of resilient fibers, matrix fibers, and mixtures thereof.

3. The composite of claim 2 wherein the resilient fibers comprise fibers selected from the group consisting of chemically stiffened fibers, anfractuous fibers, chemithermomechanical pulp fibers, prehydrolyzed kraft pulp fibers, synthetic fibers, and mixtures thereof.

4. The composite of claim 3 wherein the synthetic fibers comprise fibers selected from the group consisting of polyolefin, polyester, polyamide, and thermobondable fibers.

5. The composite of claim 4 wherein the polyester fibers comprise polyethylene terephthalate fibers.

6. The composite of claim 3 wherein the chemically stiffened fibers comprise crosslinked cellulosic fibers.

7. The composite of claim 2 wherein the matrix fibers comprise cellulosic fibers.

8. The composite of claim 7 wherein the cellulosic fibers comprise fibers selected from the group consisting of wood pulp fibers, cotton linters, cotton fibers, hemp fibers, rayon fibers, cellulose acetate fibers, and mixtures thereof.

9. The composite of claim 1 wherein the binder is selected from the group consisting of thermoplastic fibers, soluble bonding mediums, and wet strength agents.

10. The composite of claim 9 wherein the binder comprises a fibrous binding material.

11. The composite of claim 10 wherein the fibrous binding material comprises bicomponent binding fibers.

12. The composite of claim 9 wherein the binder comprises a wet strength agent.

13. The composite of claim 1 further comprising absorbent material.

14. The composite of claim 13 wherein the absorbent material comprises a superabsorbent polymer.

15. An absorbent article comprising the composite of claim 13.

16. The composite of claim 1 wherein adjacent strata have at least one different property.

17. The composite of claim 1 having a liquid-impermeable bottom surface.

18. The composite of claim 17 wherein the first stratum comprises fibers selected from the group consisting of synthetic fibers, cellulosic fibers, eucalyptus fibers, microfibrillated fibers, and mixtures thereof.

19. The composite of claim 17 wherein the first stratum has a density in the range from about 0.3 to about 0.7 g/cm$^3$.

20. An absorbent article comprising the composite of claim 17.

21. The composite of claim 1 wherein the first stratum comprises a densified stratum.

22. The composite of claim 21 wherein the densified stratum expands on liquid contact.

23. An absorbent article comprising the composite of claim 22.

24. The composite of claim 21 wherein the densified stratum comprises fibers selected from the group consisting of crosslinked cellulosic fibers, chemithermomechanical pulp fibers, and mixtures thereof.

25. The composite of claim 21 wherein the densified stratum has a density from about 0.1 to about 0.6 g/cm$^3$.

26. An absorbent article comprising the composite of claim 21.

27. The composite of claim 1 wherein the third stratum comprises a liquid-impermeable bottom surface.

28. An absorbent article comprising the composite of claim 1.

29. The absorbent article of claim 28 further comprising a liquid pervious topsheet and a liquid impervious backsheet.

30. The composite of claim 1, wherein the second stratum further comprises absorbent material.

31. The composite of claim 1, wherein the second stratum comprises a densified stratum.

32. The composite of claim 1, wherein the third stratum comprises a densified stratum.

33. An absorbent composite comprising a plurality of strata, wherein adjacent strata are separated by a transition zone intermediate and coextensive with adjacent strata, wherein each stratum comprises fibers and a binder, wherein each transition zone comprises fibers from adjacent strata commingled substantially uniformly across the composite's width and along the composite's length, and wherein the composite comprises at least three strata.

34. The composite of claim 33 wherein the composite comprises at least four strata.

35. The composite of claim 33 wherein the composite comprises at least five strata.

36. The composite of claim 33 wherein adjacent strata have at least one different property.

37. The composite of claim 33 further comprising absorbent material.

38. An absorbent article comprising the composite of claim 33.

39. The absorbent article of claim 38 further comprising a liquid pervious topsheet and a liquid impervious backsheet.

40. An absorbent composite comprising a first stratum, a second stratum, a third stratum, a first transition zone intermediate and coextensive with the first and second strata, and a second transition zone intermediate and coextensive with the second and third strata;

the first stratum comprising synthetic fibers and a binder;

the second stratum comprising crosslinked cellulosic fibers and a binder;

the third stratum comprising synthetic fibers and a binder;

the first transition zone comprising fibers from the first and second strata commingled substantially uniformly across the composite's width and along the composite's length; and the second transition zone comprising fibers from the second and third strata commingled substantially uniformly across the composite's width and along the composite's length.

41. The composite of claim 40 wherein the synthetic fibers comprise polyethylene terephthalate fibers.

42. The composite of claim 40 wherein the binder is selected from the group consisting of bicomponent binding fibers and a wet strength agent.

43. The composite of claim 40, wherein the second stratum further comprises absorbent material.

44. An absorbent composite comprising a first stratum, a second stratum, a third stratum, a first transition zone intermediate and coextensive with the first and second strata, and a second transition zone intermediate and coextensive with the second and third strata;

the first stratum comprising synthetic fibers and a binder;

the second stratum comprising crosslinked cellulosic fibers and a binder;

the third stratum comprising cellulosic fibers and a binder;

the first transition zone comprising fibers from the first and second strata commingled substantially uniformly across the composite's width and along the composite's length; and the second transition zone comprising fibers from the second and third strata commingled substantially uniformly across the composite's width and along the composite's length.

45. The composite of claim 44 wherein the synthetic fibers comprise polyethylene terephthalate fibers.

46. The composite of claim 44 wherein the binder is selected from the group consisting of bicomponent binding fibers and a wet strength agent.

47. The composite of claim 44 wherein the cellulosic fibers comprise crosslinked cellulosic fibers.

48. The composite of claim 44, wherein the second stratum comprises absorbent material.

49. An absorbent composite comprising a first stratum, a second stratum, a third stratum, a first transition zone intermediate and coextensive with the first and second strata, and a second transition zone intermediate and coextensive with the second and third strata;

the first stratum comprising cellulosic fibers and a binder;

the second stratum comprising crosslinked cellulosic fibers and a binder;

the third stratum comprising cellulosic fibers and a binder;

the first transition zone comprising fibers from the first and second strata commingled substantially uniformly across the composite's width and along the composite's length; and the second transition zone comprising fibers from the second and third strata commingled substantially uniformly across the composite's width and along the composite's length.

50. The composite of claim 49 wherein the binder is selected from the group consisting of bicomponent binding fibers and a wet strength agent.

51. The composite of claim 49 wherein the cellulosic fibers comprise polyethylene terephthalate fibers.

52. The composite of claim 49, wherein the second stratum comprises absorbent material.

53. An absorbent composite comprising a first stratum, a second stratum, a third stratum, a first transition zone intermediate and coextensive with the first and second strata, and a second transition zone intermediate and coextensive with the second and third strata;

the first stratum comprising synthetic fibers and a binder;

the second stratum comprising crosslinked cellulosic fibers, absorbent material, and a binder;

the third stratum comprising synthetic fibers and a binder;

the first transition zone comprising fibers from the first and second strata commingled substantially uniformly across the composite's width and along the composite's length; and the second transition zone comprising fibers from the second and third strata commingled substantially uniformly across the composite's width and along the composite's length.

54. The composite of claim 53 wherein the synthetic fibers comprise polyethylene terephthalate fibers.

55. The composite of claim 53 wherein the binder is selected from the group consisting of bicomponent binding fibers and a wet strength agent.

56. The composite of 53 claim wherein the absorbent material comprises a superabsorbent polymer.

57. The composite of claim 53 wherein the second stratum further comprises fluff pulp fibers.

58. The composite of claim 53 wherein the second stratum binder comprises a wet strength agent.

59. An absorbent composite comprising a first stratum, a second stratum, a third stratum, a first transition zone intermediate and coextensive with the first and second strata, and a second transition zone intermediate and coextensive with the second and third strata;

the first stratum comprising synthetic fibers and a binder;

the second stratum comprising crosslinked cellulosic fibers, absorbent material, and a binder;

the third stratum comprising cellulosic fibers and a binder;

the first transition zone comprising fibers from the first and second strata commingled substantially uniformly across the composite's width and along the composite's length; and the second transition zone comprising fibers from the second and third strata commingled substantially uniformly across the composite's width and along the composite's length.

60. The composite of claim 59 wherein the synthetic fibers comprise polyethylene terephthalate fibers.

61. The composite of claim 59 wherein the binder is selected from the group consisting of bicomponent binding fibers and a wet strength agent.

62. The composite of claim 59 wherein the cellulosic fibers comprise crosslinked cellulosic fibers.

63. The composite of claim 59 wherein the absorbent material comprises a superabsorbent polymer.

64. The composite of claim 59 wherein the second stratum further comprises fluff pulp fibers.

65. The composite of claim 59 wherein the second stratum binder comprises a wet strength agent.

66. An absorbent composite comprising a first stratum, a second stratum, a third stratum, a first transition zone intermediate and coextensive with the first and second strata, and a second transition zone intermediate and coextensive with the second and third strata;

the first stratum comprising cellulosic fibers and a binder;

the second stratum comprising crosslinked cellulosic fibers, absorbent material, and a binder;

the third stratum comprising cellulosic fibers and a binder;

the first transition zone comprising fibers from the first and second strata commingled substantially uniformly across the composite's width and along the composite's length; and the second transition zone comprising fibers from the second and third strata commingled substantially uniformly across the composite's width and along the composite's length.

67. The composite of claim 66 wherein the binder is selected from the group consisting of bicomponent binding fibers and a wet strength agent.

68. The composite of claim 66 wherein the cellulosic fibers comprise crosslinked cellulosic fibers.

69. The composite of claim 66 wherein the absorbent material comprises a superabsorbent polymer.

70. The composite of claim 66 wherein the second stratum further comprises fluff pulp fibers.

71. The composite of claim 66 wherein the second stratum binder comprises a wet strength agent.

* * * * *